(12) United States Patent
Chen et al.

(10) Patent No.: US 11,471,621 B2
(45) Date of Patent: Oct. 18, 2022

(54) ELECTRONIC VAPORIZER DEVICE, ELECTRONIC VAPORIZER DEVICE BODY, AND OPERATION METHOD

(71) Applicant: SHENZHEN RELX TECHNOLOGY CO., LTD., Shenzhen (CN)

(72) Inventors: Chen Chen, Shenzhen (CN); Hui Wang, Shenzhen (CN); Yao Fu, Shenzhen (CN); Weifeng Chen, Shenzhen (CN); Shuting Feng, Shenzhen (CN); Zugang Yang, Shenzhen (CN); Jin Zhang, Shenzhen (CN)

(73) Assignee: SHENZHEN RELX TECHNOLOGY CO., LTD., Shenzhen (CN)

( * ) Notice: Subject to any disclaimer, the term of this patent is extended or adjusted under 35 U.S.C. 154(b) by 486 days.

(21) Appl. No.: 16/579,863

(22) Filed: Sep. 24, 2019

(65) Prior Publication Data
US 2020/0405981 A1 Dec. 31, 2020

(30) Foreign Application Priority Data

Jun. 27, 2019 (CN) .......................... 201910569156.4

(51) Int. Cl.
*A61M 15/00* (2006.01)
*A61M 11/04* (2006.01)
*F17C 9/02* (2006.01)

(52) U.S. Cl.
CPC ........ *A61M 15/002* (2014.02); *A61M 11/042* (2014.02); *A61M 2205/3334* (2013.01); *A61M 2205/8206* (2013.01); *F17C 9/02* (2013.01)

(58) Field of Classification Search
CPC .............. A61M 15/002; A61M 11/042; A61M 2205/3334; A24F 47/008
See application file for complete search history.

(56) References Cited

U.S. PATENT DOCUMENTS 10,653,187 B1 * 5/2020 Doyle .................... A24F 40/42
11,227,469 B2 * 1/2022 Chen ....................... G08B 7/02
(Continued)

FOREIGN PATENT DOCUMENTS

| CN | 203943074 U | 11/2014 |
|---|---|---|
| CN | 106037023 A | 10/2016 |

(Continued)

OTHER PUBLICATIONS

European Search Report of corresponding European Patent Application No. 20159027.0 dated Sep. 18, 2020.
(Continued)

*Primary Examiner* — Neil Abrams
(74) *Attorney, Agent, or Firm* — Idea Intellectual Limited; Margaret A. Burke; Sam T. Yip

(57) ABSTRACT

The present application relates to an electronic vaporizer device, an electronic vaporizer device body, and an operation method. The electronic vaporizer device body is used in combination with an electronic vaporizer, the electronic vaporizer device body including: a power supply configured to supply power; an airflow sensor configured to detect an airflow change and output first level information; a main control circuit electrically connected to the airflow sensor and configured to control, according to the first level information, the power supply to supply or interrupt power to the electronic vaporizer.

16 Claims, 26 Drawing Sheets

(56) References Cited

U.S. PATENT DOCUMENTS

| | | | |
|---|---|---|---|
| 2013/0340750 A1* | 12/2013 | Thorens | A24F 40/50 |
| | | | 128/202.21 |
| 2017/0047756 A1 | 2/2017 | Xiang | |
| 2018/0289068 A1 | 10/2018 | Liao et al. | |
| 2019/0124989 A1 | 5/2019 | Qiu | |
| 2020/0352247 A1* | 11/2020 | Yamada | A24F 40/51 |
| 2020/0404974 A1* | 12/2020 | Chen | H04L 63/0428 |
| 2020/0405981 A1* | 12/2020 | Chen | A24F 40/53 |
| 2021/0235772 A1* | 8/2021 | Conley | A61M 11/042 |

FOREIGN PATENT DOCUMENTS

| | | |
|---|---|---|
| CN | 106473233 A | 3/2017 |
| CN | 108185527 A | 6/2018 |
| WO | 2014054035 A1 | 4/2014 |
| WO | 2014205456 A2 | 12/2014 |
| WO | 2016154815 A1 | 10/2016 |

OTHER PUBLICATIONS

International Search Report and Written Opinion of corresponding PCT Patent Application No. PCT/CN2019/093202 dated Aug. 28, 2019.

* cited by examiner

ELECTRONIC VAPORIZER DEVICE, ELECTRONIC VAPORIZER DEVICE BODY, AND OPERATION METHOD

CROSS REFERENCE TO RELATED APPLICATIONS

The present application claims the benefit of priority from the China Patent Application No. 201910569156.4, filed on 27 Jun. 2019, the disclosure of which is hereby incorporated by reference in its entirety.

BACKGROUND OF THE INVENTION

1. Field of the Invention

The present application relates to the field of vaporizer device technologies, and in particular, to an electronic vaporizer device, an electronic vaporizer device body, and an operation method.

2. Description of the Related Art

A vaporizing device refers to a device which heats a vaporizable substance that is stored to form a vaporization state, for example, an electronic cigarette for heating e-liquid or other similar substances into vapor or smoke for a user to inhale. With the continuous improvement of intelligence, how to make the electronic cigarette better meet the requirements of users and to improve user experience through intelligent means has been an indispensable part of electronic cigarette development.

SUMMARY OF THE INVENTION

According to some embodiments of the present application, provided is an electronic vaporizer device body configured to be used in combination with an electronic vaporizer, the electronic vaporizer device body including: a power supply, configured to supply power; an airflow sensor, configured to detect an airflow change and output first level information; and a main control circuit, electrically connected to the airflow sensor and configured to control, according to the first level information, the power supply to supply or interrupt power to the electronic vaporizer.

According to some embodiments of the present application, the airflow sensor outputs the first level information having a first logic level when an airflow is detected, and the main control circuit controls the power supply to supply power to the electronic vaporizer upon receiving the first level information having the first logic level.

According to some embodiments of the present application, the airflow sensor outputs the first level information having a second logic level when no airflow is detected, and the main control circuit controls the power supply to interrupt power to the electronic vaporizer upon receiving the first level information having the second logic level.

According to some embodiments of the present application, the main control circuit increases a count value when a time interval between receiving the first level information having the first logic level and the subsequent receiving of the first level information having the second logic level is detected to be greater than a first preset time.

According to some embodiments of the present application, the main control circuit controls an alerting device to operate in a first mode when a count value within a second preset time is detected to be greater than a preset threshold.

According to some embodiments of the present application, the main control circuit controls the power supply to interrupt power to the electronic vaporizer when a time interval between receiving the first level information having the first logic level and subsequent receiving of the first level information having the second logic level is detected to be greater than a third preset time.

According to some embodiments of the present application, the first logic level is a high level, and the second logic level is a low level.

According to some embodiments of the present application, the first logic level is a low level, and the second logic level is a high level.

According to some embodiments of the present application, the alerting device includes one or any combination of the following: a motor and an indicator light.

According to some embodiments of the present application, provided is an electronic vaporizer device, including an electronic vaporizer device body according to any one of the foregoing embodiments.

According to some embodiments of the present application, provided is an operation method applied to an electronic vaporizer device body, the method including: detecting an airflow change, and outputting first level information by an airflow sensor; and controlling, by a main control circuit according to the first level information, the power supply to supply or interrupt power to an electronic vaporizer.

According to some embodiments of the present application, the airflow sensor outputs the first level information having a first logic level when an airflow is detected, and the main control circuit controls the power supply to supply power to the electronic vaporizer upon receiving the first level information having the first logic level.

According to some embodiments of the present application, the airflow sensor outputs the first level information having a second logic level when no airflow is detected, and the main control circuit controls the power supply to interrupt power to the electronic vaporizer upon receiving the first level information having the second logic level.

According to some embodiments of the present application, the main control circuit increases a count value when a time interval between receiving the first level information having the first logic level and subsequent receiving of the first level information having the second logic level is detected to be greater than a first preset time.

According to some embodiments of the present application, the main control circuit controls an alerting device to operate in a first mode when a count value within a second preset time is detected to be greater than a preset threshold.

According to some embodiments of the present application, the main control circuit controls the power supply to interrupt power to the electronic vaporizer when a time interval between receiving the first level information having the first logic level and subsequent receiving of the first level information having the second logic level is detected to be greater than a third preset time.

According to some embodiments of the present application, the first logic level is a high level, and the second logic level is a low level.

According to some embodiments of the present application, the first logic level is a low level, and the second logic level is a high level.

BRIEF DESCRIPTION OF THE DRAWINGS

The following will briefly illustrate the accompanying drawings. Drawings necessary to describe the embodiments of the present application or the prior art will be briefly illustrated so as to facilitate the description of the embodiments of the present application. Obviously, the accompanying drawings described below only show some embodiments of the present application. For those skilled in the art, the drawings of other embodiments can still be obtained according to the structures illustrated in the drawings without any creative effort.

PREFERRED EMBODIMENT OF THE PRESENT INVENTION

Figure 1:
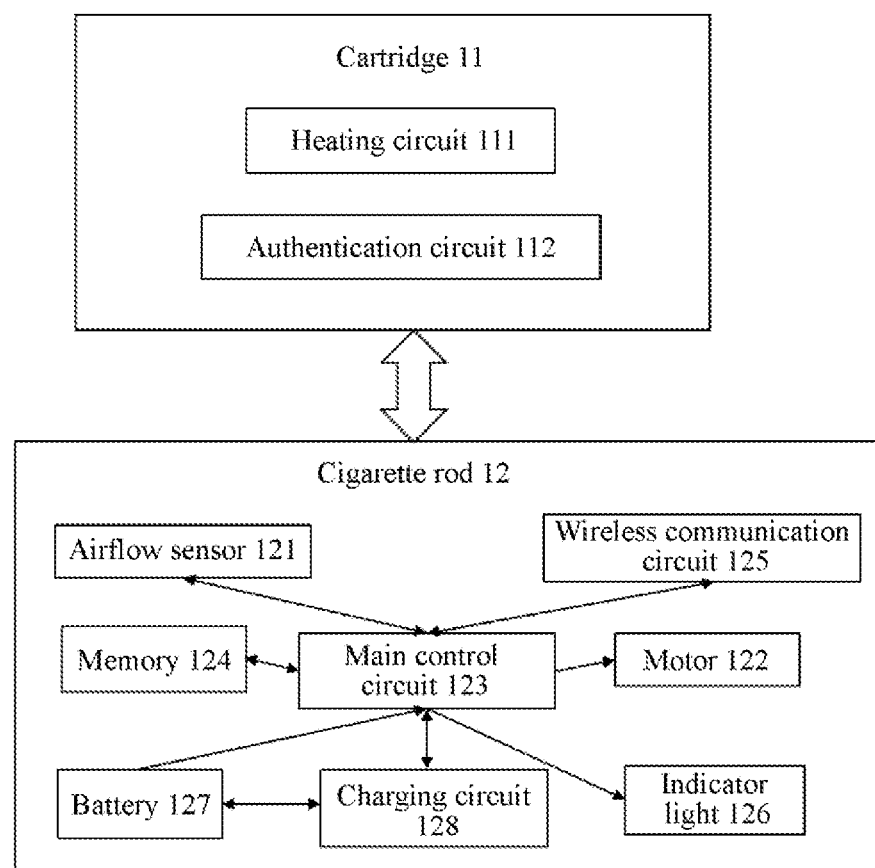
FIG. 1 is a schematic block diagram of an electronic cigarette according to some embodiments of the present application.

The embodiments of the present application will be described in detail below. Throughout the specification, the same or similar components and components having the same or similar functions are denoted by similar reference numerals. The embodiments described herein with respect to the drawings are illustrative and graphical, and are used for providing a basic understanding of the present application. The embodiments of the present application should not be interpreted as limitations to the present application.

In some embodiments of the present application, an electronic vaporizer device is also referred to as an electronic cigarette, the electronic vaporizer device including an electronic vaporizer device body and an electronic vaporizer, the electronic vaporizer device body is also referred to as a cigarette rod, and the electronic vaporizer is also referred to as a cartridge. In some embodiments of the present application, the cartridge and the cigarette rod are separate structural components, and the cartridge is connected to the cigarette rod in a pluggable manner. The cartridge is engaged with the cigarette rod to form an electronic cigarette. In some embodiments of the present application, the cartridge and the cigarette rod are integrally formed structural components.

FIG. 1 is a schematic block diagram of an electronic cigarette according to some embodiments of the present application. The electronic cigarette 10 includes a cartridge 11 and a cigarette rod 12. The cartridge 11 includes a heating circuit 111 for heating e-liquid or similar vaporizable substances stored in the cartridge 11 into a vaporization state, for the user to inhale or smoke. The cigarette rod 12 includes a main control circuit 123, an indicator light 126, and a battery 127. The battery 127 serves as a power supply configured to supply power to the electronic cigarette 10 when the electronic cigarette 11 is in operation.

In some embodiments of the present application, the cigarette rod 12 further includes a charging circuit 128. The charging circuit 128 is configured to connect to an external power supply to charge the battery 127. The charging circuit 128 includes a USB type-C (a Universal Serial Bus Interface) interface that is connected to the external power supply via the USB type-C interface to charge the battery 127. It should be noted that a specific form of the charging circuit 128 is not limited to the foregoing description.

Figures 2A, 2B:
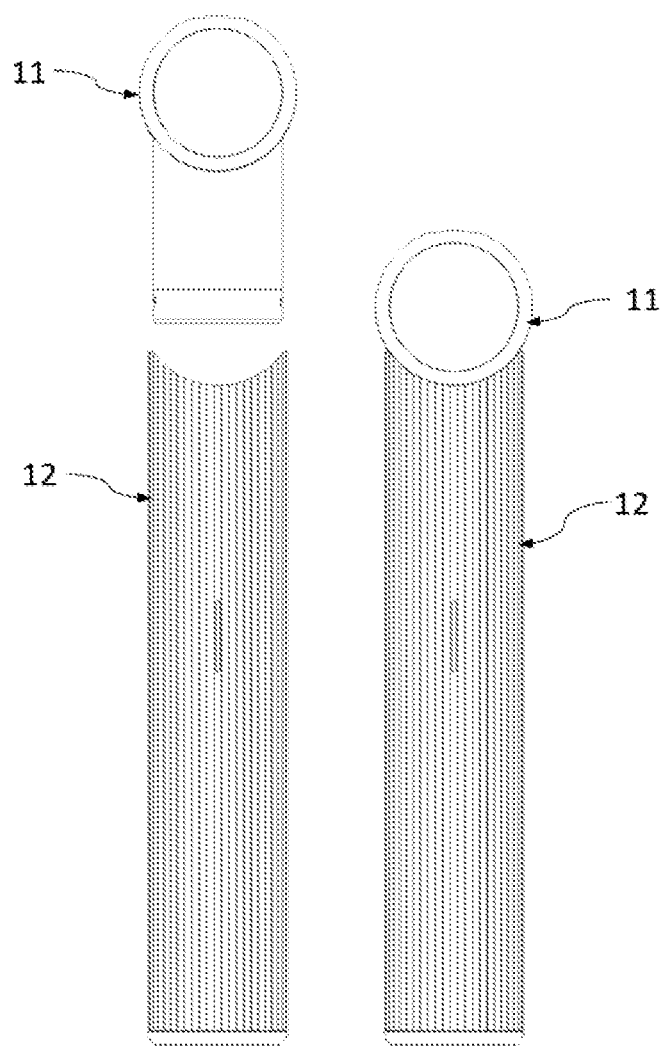
FIGS. 2A-2B are schematic diagrams of a cartridge and a cigarette rod in a disengaged state and in an engaged state respectively according to some embodiments of the present application.

FIGS. 2A-2B are schematic diagrams of a cartridge 11 and a cigarette rod 12 in an engaged state of an electronic cigarette 10 according to some embodiments of the present application. As shown in FIG. 2A, the cartridge 11 and the cigarette rod 12 are in a disengaged state. As shown in FIG. 2B, the cartridge 11 and the cigarette rod 12 are in an engaged state. The cartridge 11 is inserted into the cigarette rod 12 to form the engaged state in FIG. 2B. Because the cartridge 11 itself has resistance, when the cartridge 11 is inserted into the cigarette rod 12 and engaged with the cigarette rod 12, the cartridge 11 divides a voltage. An output level of a circuit connected to the cartridge 11 is detected to determine whether the cartridge 11 is engaged with the cigarette rod 12. Specifically, when a main control circuit 123 detects that the output level of the connection circuit is a high level, the cartridge 11 and the cigarette rod 12 are in a disengaged state. When the main control circuit 123 detects that the output level of the connection circuit is a low level, the cartridge 11 and the cigarette rod 12 are in an engaged state. The main control circuit 123 drives an indicator light 126 to operate in an alerting mode when the cartridge 11 and the cigarette rod 12 are detected to be in the engaged state. The alerting mode is: the indicator light 126 is bright and then gradually goes out, so that the user can be notified that the cartridge 11 and the cigarette rod 12 has been engaged and can be used normally. In some embodiments of the present application, the main control circuit 123 may also determine that the cartridge 11 and the cigarette rod 12 have not been engaged when the output level of the connection circuit is detected to be a low level, and determine that the cartridge 11 and the cigarette rod 12 have been engaged when the output level of the connection circuit is detected to be a high level.

It should be noted that, in the embodiment of the present application, the high level and the low level are different logic levels having relative voltage values. When the voltage is between V1 and V2, the level is high, and when the voltage is between V3 and V4, the level is low, where V1 is not less than V4. For example, 0-0.25 V may be predetermined as low level, and 3.5-5 V are predetermined as high level, but is not limited thereto and may be determined according to practical conditions.

In some embodiments of the present application, as shown in FIG. 1, the cigarette rod 12 further includes a motor 122. The main control circuit 123 controls, when the cartridge 11 and the cigarette rod 12 are detected to be in an engaged state, the motor 122 to operate in an alerting mode, that is, the motor 122 vibrates after a time T1. For example, the motor 122 may be controlled to vibrate once every 0.5 s after the cartridge 11 and the cigarette rod 12 are in an engaged state, and the vibration time is 40 ms. The time and manner for vibration of the motor 122 are not limited to the foregoing description, and may be selected according to practical conditions. The motor 122 is vibrated to inform the user that the cartridge 11 and the cigarette rod 12 have been engaged and can be used normally. It should be noted that both the motor 122 and the indicator light 126 belong to the alerting device for alerting, in different modes, the user that the electronic cigarette is operating in different states. The alerting device may also include other alerting devices, for example, a display screen may be provided in the electronic cigarette 10 to alert the user by using an icon, a dynamic image, a text, or the like. In some embodiments of the present application, the alerting device further includes an acoustic generator and a vibrator.

In some embodiments of the present application, the cartridge 11 further includes an authentication circuit 112. When the cartridge 11 and the cigarette rod 12 are in a disengaged state, the main control circuit 123 is non-electrically connected to the authentication circuit 112. When the cartridge 11 and the cigarette rod 12 are in an engaged state, the main control circuit 123 is electrically connected to the authentication circuit 112. The authentication circuit 112 includes a resistor that indicates flavor information of the cartridge 11. When the cartridge 11 and the cigarette rod 12 are in an engaged state, the foregoing connection pin of the main control circuit 123 and the resistor form an electrical connection loop. Depending on different resistance values of the resistor in each cartridge 11, the main control circuit 123 determines that a level of the connection pin corresponding to the resistor, and determines the cartridge 11 of different flavors according to different levels. For example, when the resistance is 2 ohms, it indicates that a grapefruit-flavor cartridge 11 is engaged with the cigarette rod 12. When the resistance is 4 ohms, it indicates that a mint-flavor cartridge 11 is engaged with the cigarette rod 12. It should be noted that a resistance value of a specific resistor and the flavor of the corresponding cartridge 11 are not limited thereto, which can be determined according to practical conditions.

In some embodiments of the present application, as shown in FIG. 1, the cigarette rod 12 further includes an airflow sensor 121. The airflow sensor 121 is electrically connected to the main control circuit 123. In some embodiments of the present application, the main control circuit 123 enables the airflow sensor 121 when the output level of the connection circuit is detected to be a high level. In some embodiments of the present application, the main control circuit 123 enables the airflow sensor 121 when the output level of the connection circuit is detected to be a low level. Enabling the airflow sensor 121 may refer to supplying power to the airflow sensor 121, or may refer to initializing the airflow sensor 121 to prepare the airflow sensor 121 for normal detection.

In some embodiments of the present application, when the cartridge 11 and the cigarette rod 12 are in an engaged state, the user can smoke or inhale normally. The airflow sensor 121 detects an airflow change when the user performs a vaping action. When the airflow sensor 121 detects the airflow, that is, when the air flows or changes, the airflow sensor 121 outputs a high level, that is, it indicates that the user is vaping. In this case, the main control circuit 123 controls a heating circuit 111 to perform heating to vaporize the e-liquid. When the airflow sensor 121 does not detect the airflow, that is, when no air flows or changes, the airflow sensor 121 outputs a low level, that is, it indicates that the user has stopped vaping. Then the main control circuit 123 controls a heating circuit 111 to stop heating. The main control circuit 123 records a start time t2 at which the high level is generated when the low level is detected to be converted into the high level, and records a start time t3 at which the low level is generated when the high level is detected to be converted into the low level next time. A time T2=t3−t2 for which the user takes one puff, where t3 is greater than t2. The main control circuit 123 performs counting and increases a count value C1 when T2 is greater than a preset threshold t4, for example, the count value may increase by 1, t4 may be set to 1 s, but is not limited thereto. When the count value C1 within a preset time T3 is greater than a preset threshold n, the main control circuit 123 drives the motor 122 and the indicator light to operate in the alerting mode. The alerting mode is: the motor 122 vibrates. For example, when the count value C1 is greater than 15 within 10 minutes of T3, the main control circuit 123 may drive the motor 122 to vibrate once for one second after the 15th puff with a vibration time of 40 ms, thereby effectively alerting the user to control the vaping amount and preventing excessive vaping.

In some embodiments of the present application, the airflow sensor 121 may also output a low level when the airflow is detected, and outputs a high level when no airflow is detected. The main control circuit 123 may determine whether the user is smoking according to level information that has different logic levels output by the airflow sensor 121, and the specific determining manner is not limited to the foregoing.

In some embodiments of the present application, the main control circuit 123 disconnects the power supply from the battery 127 to the heating circuit 111 when T2 is greater than t5, so that the heating circuit 111 stops heating. For example, the control circuit 123 disconnects the power supply from the battery 127 from the heating circuit 111 when T2 is greater than 5 s, so that the heating circuit 111 stops heating. In this way, the user can be prevented from smoking excessively.

In some embodiments of the present application, as shown in FIG. 1, the cigarette rod 12 further includes a memory 124 and a wireless communication circuit 125, both the memory 124 and the wireless communication circuit 125 being electrically connected to the main control circuit 123. The memory 124 may be configured to store information and be read and written. The memory 124 stores smoking information, the smoking information including an ID of the cartridge 11, the number of puffs, smoking time, and the like.

The wireless communication circuit 125 is used for performing wireless communication. The wireless communication may use one or more of the following modes: Bluetooth, Wi-Fi, the 3rd generation (3G) mobile communication technology, the 4th generation (4G) mobile communication technology, the 5th generation (5G) mobile communication technology, near field communication, ultrasonic communication, ZigBee (ZigBee protocol), radio frequency identification (RFID), and the like. The main control circuit 123 interacts with an intelligent terminal through the wireless communication circuit 125. The intelligent terminal includes a mobile phone, a computer, an intelligent wearable apparatus (for example, an intelligent watch), a tablet, and the like.

Figure 3:
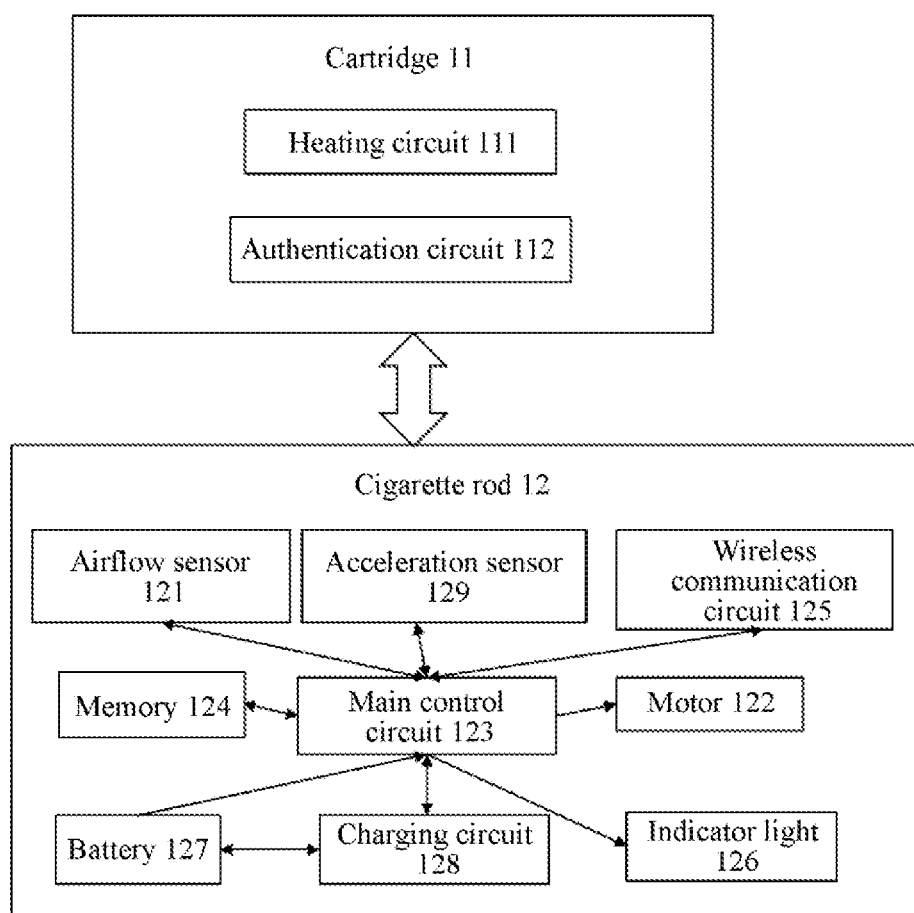
FIG. 3 is a schematic block diagram of an electronic cigarette according to some embodiments of the present application.

In some embodiments of the present application, as shown in FIG. 3, the cigarette rod 12 further includes an acceleration sensor 129, the acceleration sensor 129 being electrically connected to the main control circuit 123. In some embodiments of the present application, the main control circuit 123 enables the acceleration sensor 129 when the output level of the connection circuit is detected to be a high level. In some embodiments of the present application, the main control circuit 123 enables the airflow sensor 129 when the output level of the connection circuit is detected to be a low level. Enabling the acceleration sensor 129 may refer to supplying power to the airflow sensor 129, or may refer to initializing the acceleration sensor 129 to prepare the acceleration sensor 129 for normal detection.

In some embodiments of the present application, the main control circuit 123 obtains acceleration information of the acceleration sensor 129, and enables the wireless communication circuit 125 when an acceleration value included in the acceleration information is greater than a preset threshold a1. The acceleration value includes at least one of an acceleration value in an X-axis direction, an acceleration value in a Y-axis direction, or an acceleration value in a Z-axis direction in a coordinate system. The acceleration sensor 129 is a G-sensor (a gravity sensor), but is not limited thereto. A case that the acceleration value is greater than the preset threshold a1 may indicate that the user is shaking the electronic cigarette 10. For example, when the wireless communication circuit 125 includes a Bluetooth module and performs wireless communication using the Bluetooth module, the main control circuit 123 enables the Bluetooth module when the obtained acceleration value is greater than the preset threshold a1, and sends a broadcast signal through the Bluetooth module. In addition, the main control circuit 123 is further configured to operate in a fourth driving mode when the obtained acceleration value is greater than the preset threshold a1 and the count value C1 is increased, and the fourth driving mode is: controlling the indicator light 126 to flash 15 times, to remind the user that the Bluetooth mode of the electronic cigarette 10 is enabled. In addition, if the user performs the shaking action again, the indicator light 126 will flash again 15 times. In this case, the user may perform Bluetooth matching with the electronic cigarette 10 through the intelligent terminal, and perform Bluetooth communication after the matching is performed successfully. The main control circuit 123 may send or transmit the smoking information stored in the memory 124 to the intelligent terminal through Bluetooth communication. A dedicated application (APP) of the intelligent terminal performs data analysis according to the received smoking information to better guide the user to control smoking, reduce or quit smoking.

In some embodiments of the present application, the authentication circuit 112 includes an encryption chip (not shown in the figure). The encryption chip stores encrypted data information of the cartridge 11, the data information including a unique ID number, a flavor of the cartridge, an amount of tar of the cartridge, and the like. The main control circuit 123 includes a decryption module corresponding to the encryption chip, and the decryption module includes a decryption chip. The decryption module is configured to decrypt the encrypted information when the cartridge 11 and the cigarette rod 12 are in an engaged state, send or transmit decryption success information when the decryption is successful, and send or transmit decryption failure information when the decryption fails. Upon receiving the decryption failure information, the main control circuit 123 disconnects the battery 127 from the heating circuit 111. If the decryption success message is received, the main control circuit 123 drives the indicator light 126 to flash three times and drives the motor 123 to vibrate for a short time three times. The main control circuit 123 enables the Bluetooth module to transmit the broadcast signal after successfully decrypting the encrypted data information obtained from the encryption chip.

Figure 4:
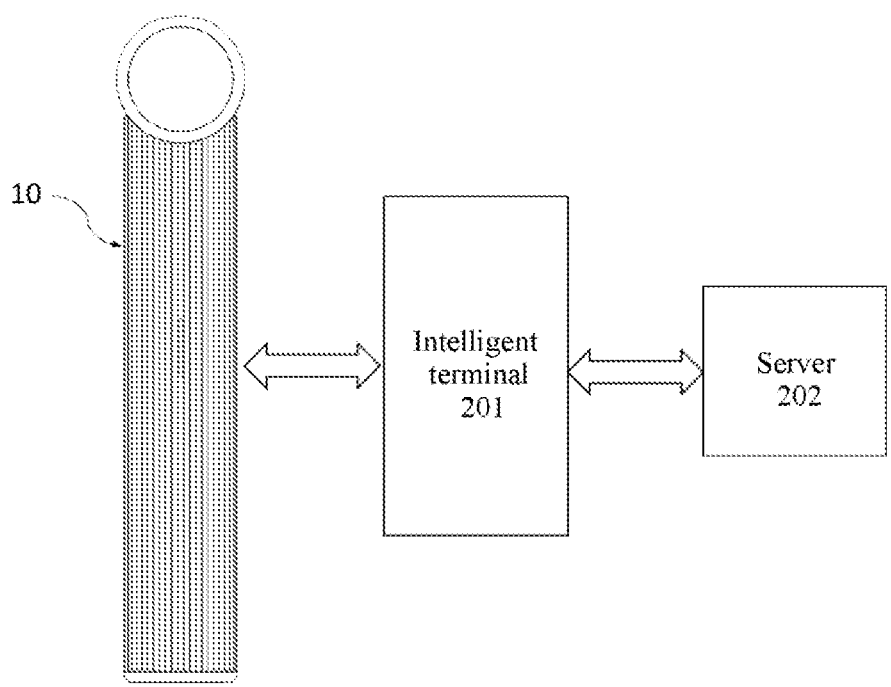
FIG. 4 is a schematic diagram of interaction between an electronic cigarette and an intelligent terminal according to some embodiments of the present application.

FIG. 4 is a schematic diagram of interaction between an electronic cigarette 10 and an intelligent terminal according to some embodiments of the present application. An intelligent terminal 201 turns on the Bluetooth and matches the electronic cigarette 10, and receives the data information sent or transmitted by the electronic cigarette 10 after the matching is successful. The intelligent terminal 201 sends or transmits the foregoing data information to a server 202, and the server 202 is configured to send analyzed and processed information about the electronic cigarette 10 to the intelligent terminal 201. The intelligent terminal 201 displays the data information of the cartridge 11 by the dedicated APP, including information such as the flavor of the cartridge, the number of puffs per day, the number of puffs per week, the number of puffs per month, the number of accumulated puffs, and an amount of remaining e-liquid, which are displayed as a graph. The amount of remaining e-liquid may be obtained according to the number of accumulated puffs for the cartridge 11.

In some embodiments of the present application, when the electronic cigarette 10 and the intelligent terminal 201 are in a Bluetooth connection state, the "stop heating" touch control widget on the dedicated APP is activated by the user, and the intelligent terminal 201 obtains the "stop heating" instruction, and transmits the "stop heating" instruction to the main control circuit 123 via a Bluetooth communication link. Upon receiving the "stop heating" instruction, the main control circuit 123 disconnects the power supply from the battery 127 to the heating circuit 111, and the heating circuit 111 stops heating. Even if the airflow sensor 121 detects the airflow and outputs a high level, that is, the user is vaping, the heating circuit 111 is not powered either; that is, the heating circuit 111 cannot heat the e-liquid.

Figure 5:
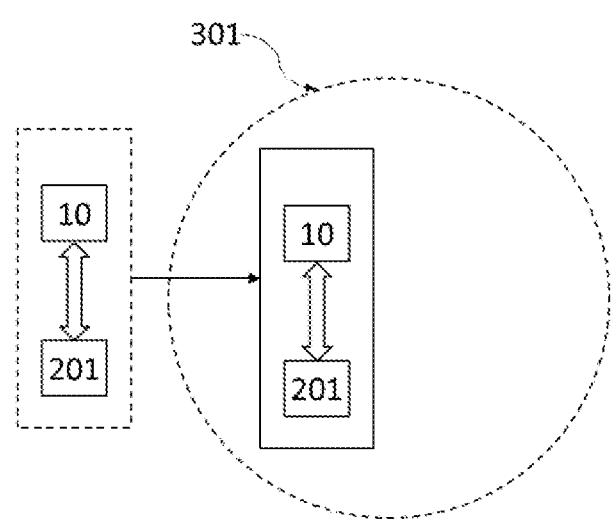
FIG. 5 is a schematic structural diagram of an electronic cigarette and an intelligent terminal in an engaged state entering a virtual geofence according to some embodiments of the present application.

In some embodiments of the present application, the electronic cigarette 10 is also prohibited or forbidden from being used in a non-smoking area. The intelligent terminal 201 has a locating or positioning function. When the user carries the intelligent terminal 201 and the electronic cigarette 10 into a virtual geofence 301, as shown in FIG. 5, the intelligent terminal 201 and the electronic cigarette 10 are in a Bluetooth connection state. The intelligent terminal 201 automatically receives a notification of "entering the fence". The intelligent terminal 201 sends a "no smoking" instruction to the electronic cigarette 10 when determining that a current location is within the geofence 301, that is, belongs to the non-smoking area. The main control circuit 123 of the electronic cigarette 10 is switched to the "no smoking" mode upon receiving the "no smoking" instruction, that is, disconnects the electrical connection between the battery 127 and the heating circuit 111, and the heating circuit 111 is prohibited or forbidden from enabling the heating function, and does not respond to level information output by the airflow sensor 121. In other words, even if the airflow sensor 121 detects the airflow and outputs a high level, that is, the user is vaping, the heating circuit 111 is not powered either, that is, the heating circuit 111 cannot heat the e-liquid. Therefore, even if the user performs the vaping action on the electronic cigarette 10 after entering the non-smoking area, the electronic cigarette 10 would not heat the e-liquid to form an atomized state, so that the user can be effectively prevented from illegally smoking.

The geofence 301 may be a virtual geographic boundary defined using any geofence technology, for example, an airport, a gas station, a mall, and the like. In addition, if the intelligent terminal 201 enters the geofence 301 and the intelligent terminal 201 determines that the geofence 301 does not belong to the non-smoking area, the "no smoking" instruction would not be sent to the electronic cigarette 10.

Figure 6:
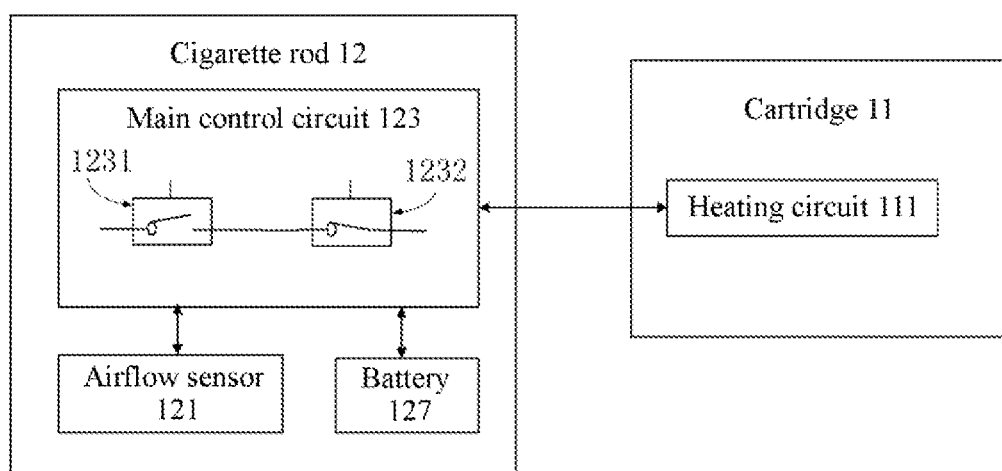
FIG. 6 is a schematic block diagram of an electronic cigarette according to some embodiments of the present application.

Specifically, as shown in FIG. 6, the main control circuit 123 includes a switch 1231 and a switch 1232. The switch 1231 and the switch 1232 are connected in series and are disposed in a circuit between the battery 127 and the heating circuit 111. When both the switch 1231 and the switch 1232 are switched or turned on, the battery 127 supplies power to the heating circuit 111 normally, causing the heating circuit 111 to heat the e-liquid. When at least one of the switch 1231 and the switch 1232 is switched or turned off, the battery 127 and the heating circuit 111 are in an open circuit state, and the heating circuit 111 would not perform heating. In some embodiments of the present application, the main control circuit 123 controls switching or turning the switch 1231 on when the no-smoking instruction is not received and the current location is detected to not belong to first location information, and controls switching or turning the switch 1232 on when determining that the received output level of the connection circuit is a high level, and the battery 124 supplies power to the cartridge 11 when both the switch 1231 and the switch 1232 are switched or turned on. In some embodiments of the present application, the main control circuit 123 controls switching or turning the switch 1231 on when the no-smoking instruction is not received and the current location is detected to not belong to first location information, and controls switching or turning the switch 1232 on when determining that the received output level of the connection circuit is a low level, and the battery 124 supplies power to the cartridge 11 when both the switch 1231 and the switch 1232 are switched or turned on.

The main control circuit 123 controls, using control pins of the switch 1231 and the switch 1232, the switch 1231 and the switch 1232 to be switched on or off. The switch 1231 remains switch-on by default. When receiving the "no smoking" instruction, the main control circuit 123 controls the switch 1231 to be switched from the switch-on state to the switch-off state, that is, the electronic cigarette 10 is switched to the "no smoking" mode. Even if the airflow sensor 121 detects the airflow and outputs a high level, that is, the user is vaping, the main control circuit 123 switches the switch 1232 off according to a high level signal, and the battery 127 and the heating circuit 111 are still in a switch-off state. In this case, the heating circuit 111 does not perform heating.

When the main control circuit 123 does not receive the "no smoking" instruction, the switch 1231 is in a switch-on state. When the airflow sensor 121 detects the airflow and outputs a high level, that is, when the user is vaping, the main control circuit 123 switches the switch 1232 on according to the high level signal. In this case, because both the switch 1231 and the switch 1232 are switched on, the battery 127 normally supplies power to the heating circuit 111, so that the heating circuit 111 heats the e-liquid, and the user can normally vape via the electronic cigarette 10.

Figure 7:
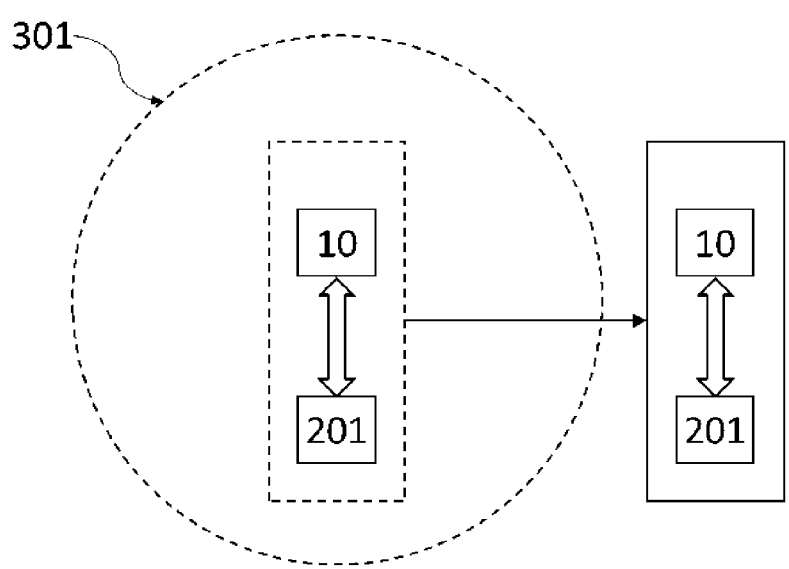
FIG. 7 is a schematic structural diagram of an electronic cigarette and an intelligent terminal in an engaged state leaving a virtual geofence according to some embodiments of the present application.

As shown in FIG. 7, when the intelligent terminal 201 and the electronic cigarette 10 leave the geofence 301 belonging to the non-smoking area, the intelligent terminal 201 automatically receives the notification of "leaving the fence" and sends an "allow smoking" instruction to the electronic cigarette 10. The main control circuit 123 of the electronic cigarette 10 is switched to an "allow smoking" mode upon receiving the "allow smoking" instruction. That is, when the main control circuit 123 is switched to the "allow smoking" mode, the airflow sensor 121 detects the airflow and outputs a high level, that is, it indicates that the user is vaping, and the main control circuit 123 controls the heating circuit 111 to heat the e-liquid to vaporize the e-liquid.

Figure 8:
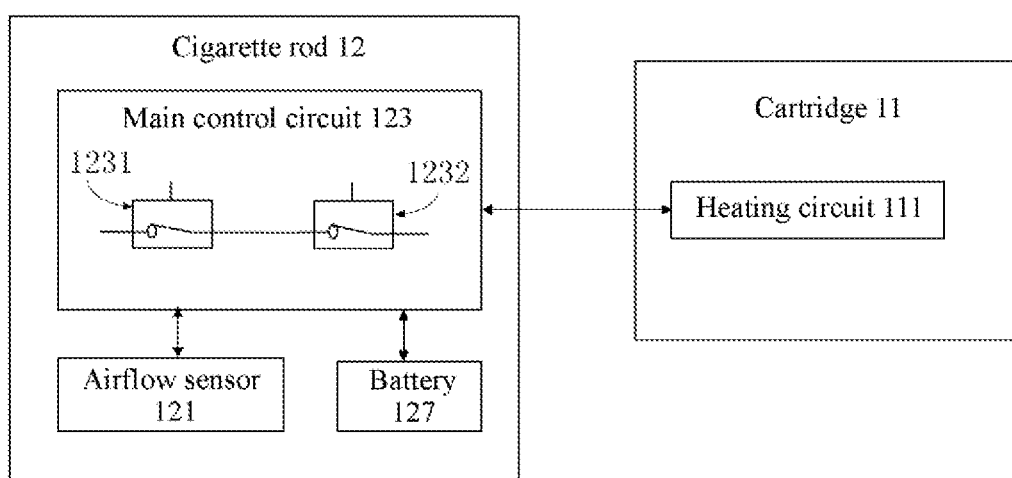
FIG. 8 is a schematic block diagram of an electronic cigarette according to some embodiments of the present application.

Specifically, as shown in FIG. 8, the main control circuit 123 switches the switch 1231 from the switch-off state to the switch-on state upon receiving the "allow smoking" instruction, that is, the electronic cigarette 10 is switched to the "allow smoking" mode. In this case, when the airflow sensor 121 detects the airflow and outputs a high level, that is, it indicates that the user is vaping normally, and the main control circuit 123 switches the switch 1232 to the switch-on state according to the high level signal. Because both the switch 1231 and the switch 1232 are in the switch-on state, the battery 127 normally supplies power to the heating circuit, so that the heating circuit 111 heats the e-liquid to form a vaporized state, and the user can normally vape via the electronic cigarette 10.

Figure 9:
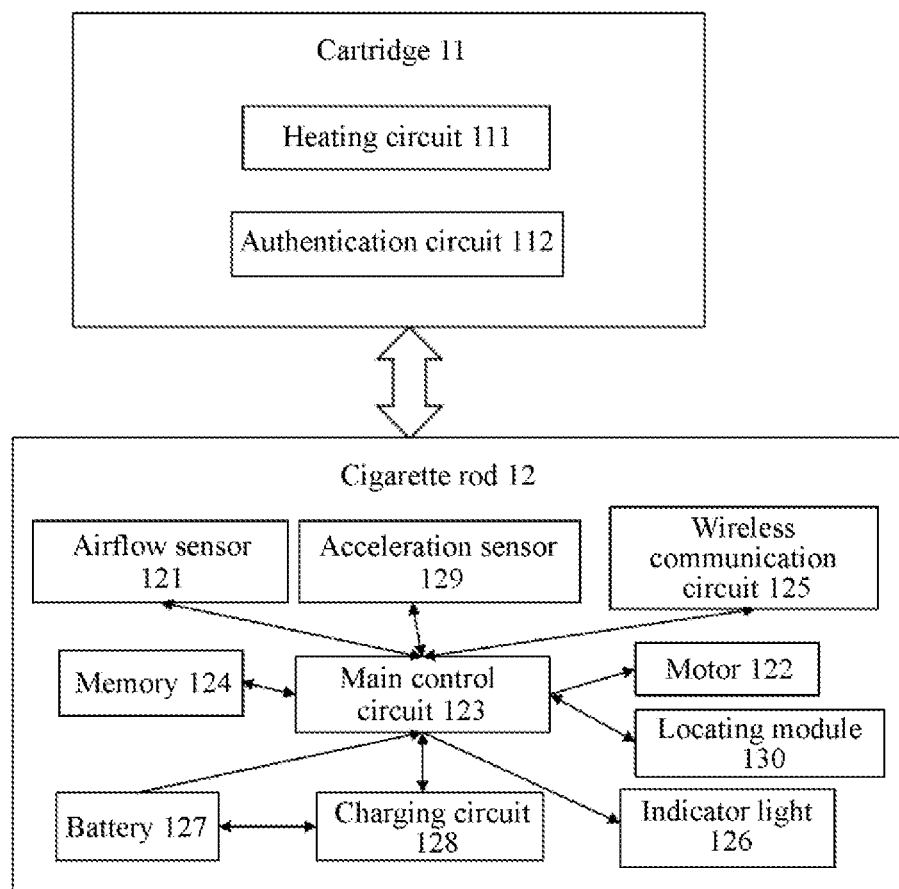
FIG. 9 is a schematic block diagram of an electronic cigarette according to some embodiments of the present application.

FIG. 9 is a schematic block diagram of an electronic cigarette 10 according to some embodiments of the present application. A cigarette rod 12 further includes a positioning module 130. The positioning module 130 is electrically connected to a main control circuit 123. The positioning module 130 has a locating or positioning function and is configured to obtain location or position information. The positioning module 130 includes a Global Positioning System (GPS) positioning module, a BeiDou positioning module, a Global Navigation Satellite System (GLONASS) positioning module, or the like.

Figures 10A, 10B:
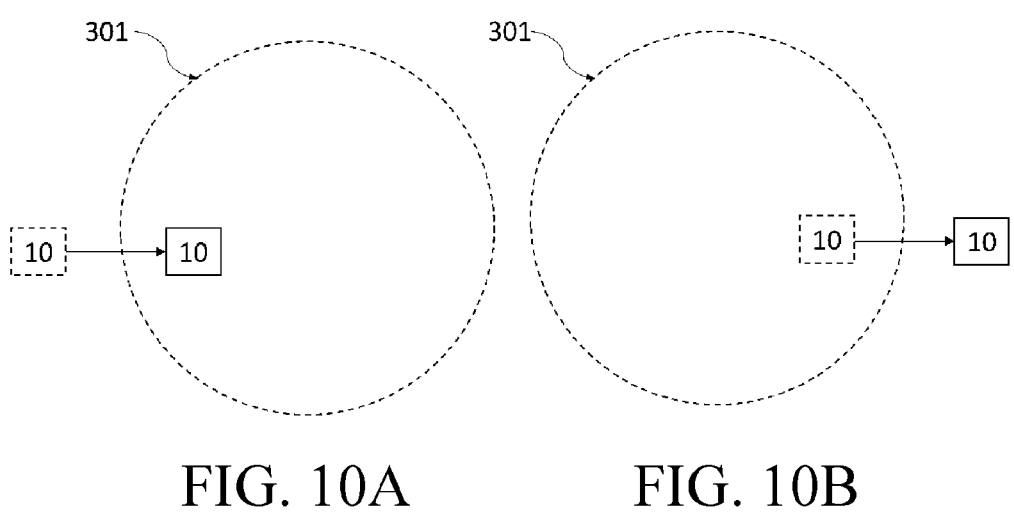
FIGS. 10A-10B are schematic block diagrams of an electronic cigarette entering a virtual geofence and leaving a virtual geofence according to some embodiments of the present application.

In some embodiments of the present application, when a user carries the electronic cigarette 10 as shown in FIG. 9 into a geofence 301, as shown in FIG. 10A, after the electronic cigarette 10 automatically receives, through the wireless communication circuit 125, a notification of "entering the fence" sent by the geofence 301, the main control circuit 123 determines that a current location is within the geofence 301, that is, after the current location belongs to non-smoking area information, a heating circuit 111 is prohibited from heating. Even if an airflow sensor 121 detects the airflow and outputs a high level, that is, when the user is vaping, the heating circuit 111 is not powered either, that is, the heating circuit 111 cannot heat the e-liquid.

Referring back to FIG. 6, the switch 1231 remains in the switch-on state by default. When determining that the current location is within the geofence 301, that is, after the current location belongs to the non-smoking area, the main control circuit 123 controls the switch 1231 to be switched from the switch-on state to the switch-off state, that is, the electronic cigarette 10 is switched to the "no smoking" mode. Even if the airflow sensor 121 detects the airflow and outputs a high level, that is, the user is vaping, the main control circuit 123 switch off the switch 1232 according to a high level signal, and the battery 127 and the heating circuit 111 are still in an open circuit state. In this case, the heating circuit 111 would not perform heating.

When determining that the current location is outside the geofence 301, that is, the current location does not belong to the non-smoking area, the main control circuit 123 maintains the switch 1231 in the switch-on state. When the airflow sensor 121 detects the airflow and outputs a high level, that is, when the user is vaping, the main control circuit 123 closes the switch 1232 according to the high level signal. In this case, because both the switch 1231 and the switch 1232 are switched on, the battery 127 normally supplies power to the heating circuit 111, so that the heating circuit 111 heats the e-liquid, and the user can normally vape via the electronic cigarette 10.

When the user carries the electronic cigarette 10 as shown in FIG. 9 away from the geofence 301 belonging to the non-smoking area, as shown in FIG. 10B, after the electronic cigarette 10 automatically receives, through a wireless communication circuit 125, a notification of "leaving the fence" sent by the geofence 301, the main control circuit 123 is switched to an "allow smoking" mode. That is, when the main control circuit 123 is switched to the "allow smoking" mode, the airflow sensor 121 detects the airflow and outputs a high level, that is, it indicates that the user can vape, and the main control circuit 123 controls the heating circuit 111 to heat the e-liquid to vaporize the e-liquid.

Referring back to FIG. 8, the main control circuit 123 switches the switch 1231 from the switch-off state to the switch-on state upon receiving the notification of "leaving the fence", that is, the electronic cigarette 10 is switched to the "allow smoking" mode. In this case, when the airflow sensor 121 detects the airflow and outputs a high level, that is, it indicates that the user can vape normally, the main control circuit 123 switches the switch 1232 to the switch-on state according to the high level signal. Because both the switch 1231 and the switch 1232 are in the switch-on state, the battery 127 normally supplies power to the heating circuit, so that the heating circuit 111 heats the e-liquid to form the vaporization state, and the user can normally vape via the electronic cigarette 10.

Figure 11:
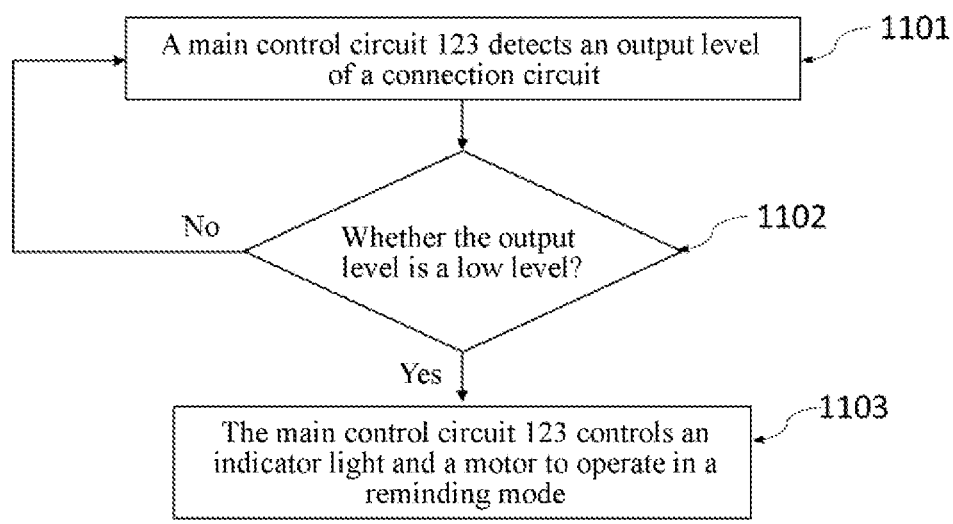
FIG. 11 is a flowchart of an operation method of an electronic cigarette according to some embodiments of the present application.

FIG. 11 is a flowchart of an operation method according to some embodiments of the present application. The operation method in FIG. 11 is used for the electronic cigarette 10 in one or more of the foregoing embodiments.

In step 1101, the main control circuit 123 detects an output level of a connection circuit. The connection circuit is a circuit for being connected to a cartridge 11. Because the cartridge 11 itself is provided with resistance, when the cartridge 11 is inserted into the cigarette rod 12 and engaged with the cigarette rod 12, the cartridge 11 generates a divided voltage in the connection circuit. It may be determined, according to the output level of the connection circuit, whether the cartridge 11 is engaged with the cigarette rod 12.

In step 1102, it is determined whether the output level is a low level. If yes, go to step 1103; if no, indicating that the cartridge 11 is not engaged with the cigarette rod 12 and going back to step 1101, the main control circuit 123 continuously detects the output level of the connection circuit.

In step 1103, the main control circuit 123 drives an indicator light 126 and a motor 122 to operate in an alerting mode. The alerting mode is that: the indicator light 126 is turned on after the cartridge 11 is engaged with the cigarette rod 12, and gradually goes out; and the motor 122 vibrates once after the cartridge 11 is engaged with the cigarette rod 12 for 0.5 s, with a vibration time of 40 ms. The alerting mode is not limited thereto, which can be set according to practical conditions. In this way, the user can be reminded or informed that the cartridge 11 has been engaged with the cigarette rod 12 to be used normally.

Figure 12:
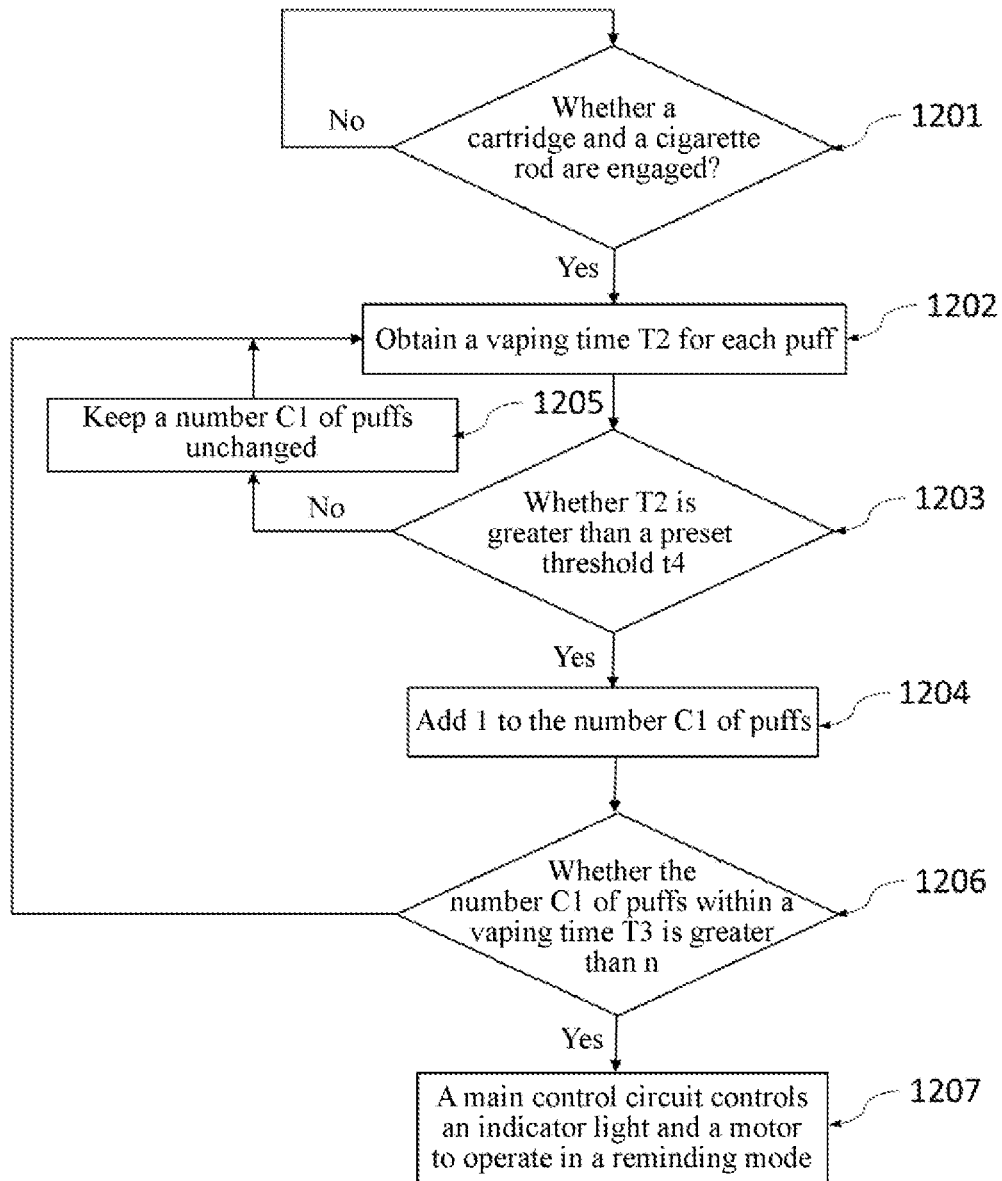
FIG. 12 is a flowchart of an operation method of an electronic cigarette according to some embodiments of the present application.

FIG. 12 is a flowchart of an operation method according to some embodiments of the present application. The operation method in FIG. 12 may be used for the electronic cigarette 10 in one or more of the foregoing embodiments.

In step 1201, the main control circuit 123 detects whether the cartridge 11 is engaged with the cigarette rod 12. If yes, go to step 1202; or if no, continue performing the detection.

In step 1202, the main control circuit 123 obtains a vaping time T2 from when the user takes a puff. Specifically, when the airflow sensor 121 detects an airflow, the airflow sensor 121 outputs a high level, that is, it indicates that the user is vaping, and in this case, the main control circuit 123 controls a heating circuit 111 to perform heating to vaporize the e-liquid. When the airflow sensor 121 does not detect an airflow, the airflow sensor 121 outputs a low level, that is, it indicates that the user has stopped vaping, and the main control circuit 123 controls the heating circuit 111 to stop heating. The main control circuit 123 records a start time t2 at which the high level is generated when the low level is detected and changed to the high level, and records a start time t3 at which the low level is generated when the high level is detected and changed to the low level. The vaping time T2=t3−t2 for which the user takes each puff, where t3 is greater than t2.

In step 1203, the main control circuit 123 detects whether the vaping time T2 for which the user takes each puff is greater than a preset threshold t4. If yes, go to step 1204. If no, go to step 1205 to keep the number C1 of vaping puffs unchanged.

In step 1204, add 1 to the number C1 of vaping puffs. In step 1205, keep the number C1 of vaping puffs unchanged.

In step 1206, the main control circuit 123 determines whether the number C1 of vaping puffs within a vaping time T3 is greater than a preset threshold n. If C1 is greater than n, go to step 1207; or if C1 is less than n, go back to step 1202.

In step 1207, the main control circuit 123 drives a motor 122 to operate in an alerting mode. The alerting mode is: the motor 122 vibrates once, and a vibration time is 40 ms. The alerting mode is not limited thereto. In this way, the alerting mode may be configured to remind or inform a user to control the vaping amount to prevent excessive smoking.

Figure 13:
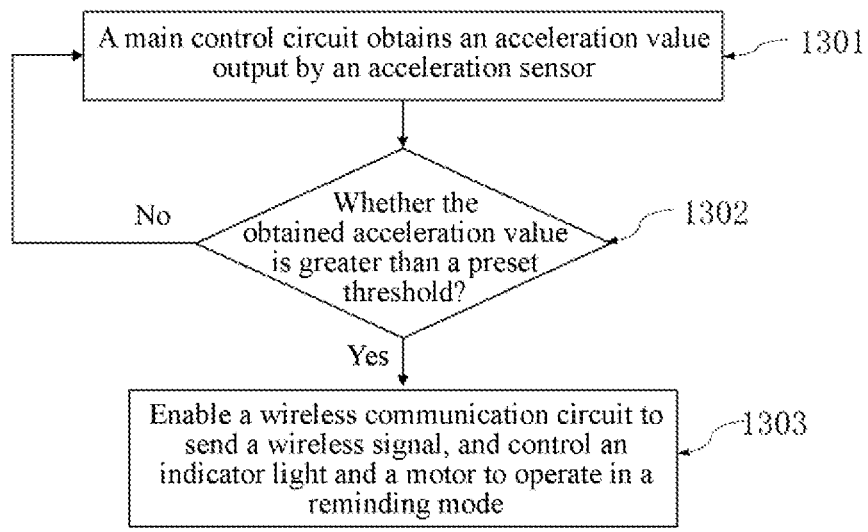
FIG. 13 is a flowchart of an operation method of an electronic cigarette according to some embodiments of the present application.

FIG. 13 is a flowchart of an operation method according to some embodiments of the present application. The operation method in FIG. 13 may be used for the electronic cigarette 10 in one or more of the foregoing embodiments.

In step 1301, the main control circuit 123 obtains an acceleration value of the acceleration sensor 129. The acceleration value may include at least one of an acceleration value in an X-axis direction, an acceleration value in a Y-axis direction, or an acceleration value in a Z-axis direction in a coordinate system. The acceleration sensor 129 is a G-sensor (a gravity sensor), but is not limited thereto.

In step 1302, the main control circuit 123 determines whether the obtained acceleration value is greater than a preset threshold. If yes, it indicates that the user is shaking the cigarette rod 12, and proceeds to step 1303; or if no, goes back to step 1301.

In step 1303, the main control circuit 123 enables the wireless communication circuit 125 to transmit a wireless signal, and drives the indicator light 126 to operate in the alerting mode.

Specifically, the wireless communication circuit 125 may include the Bluetooth module, and the main control circuit 123 enables the Bluetooth module when performing wireless communication by using the Bluetooth module and when the obtained acceleration value is greater than the preset threshold, and sends or transmits the broadcast signal through the Bluetooth module. In addition, a third alerting mode is when the indicator light 126 flashes for 15 times, to remind the user that a Bluetooth mode of an electronic cigarette 10 is enabled. In addition, if the user performs the shaking action again, the indicator light 126 will flash again for 15 times.

Figure 14:
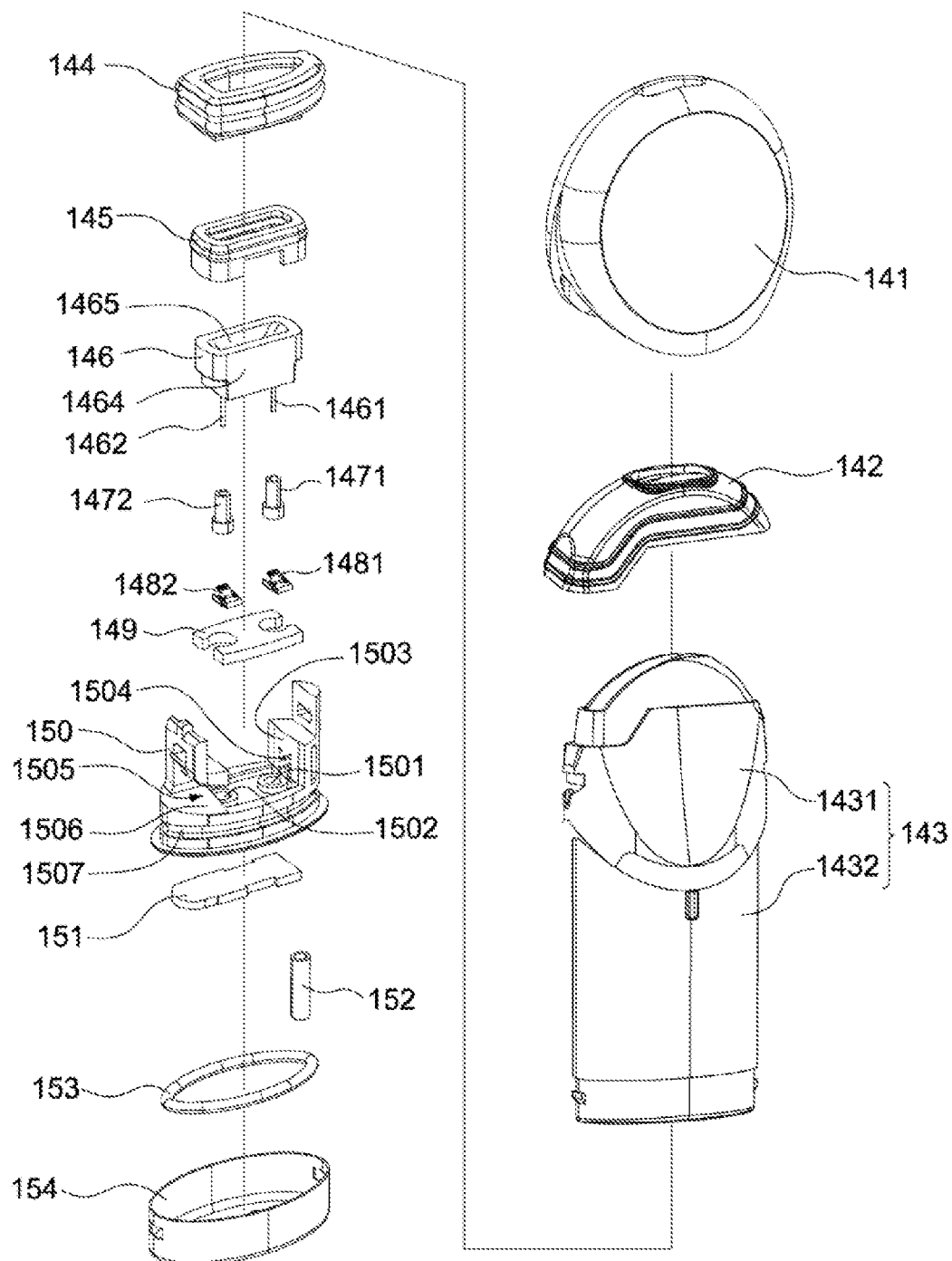
FIG. 14 is a schematic diagram of a disassembly structure of a cartridge according to some embodiments of the present application.
Figure 16:
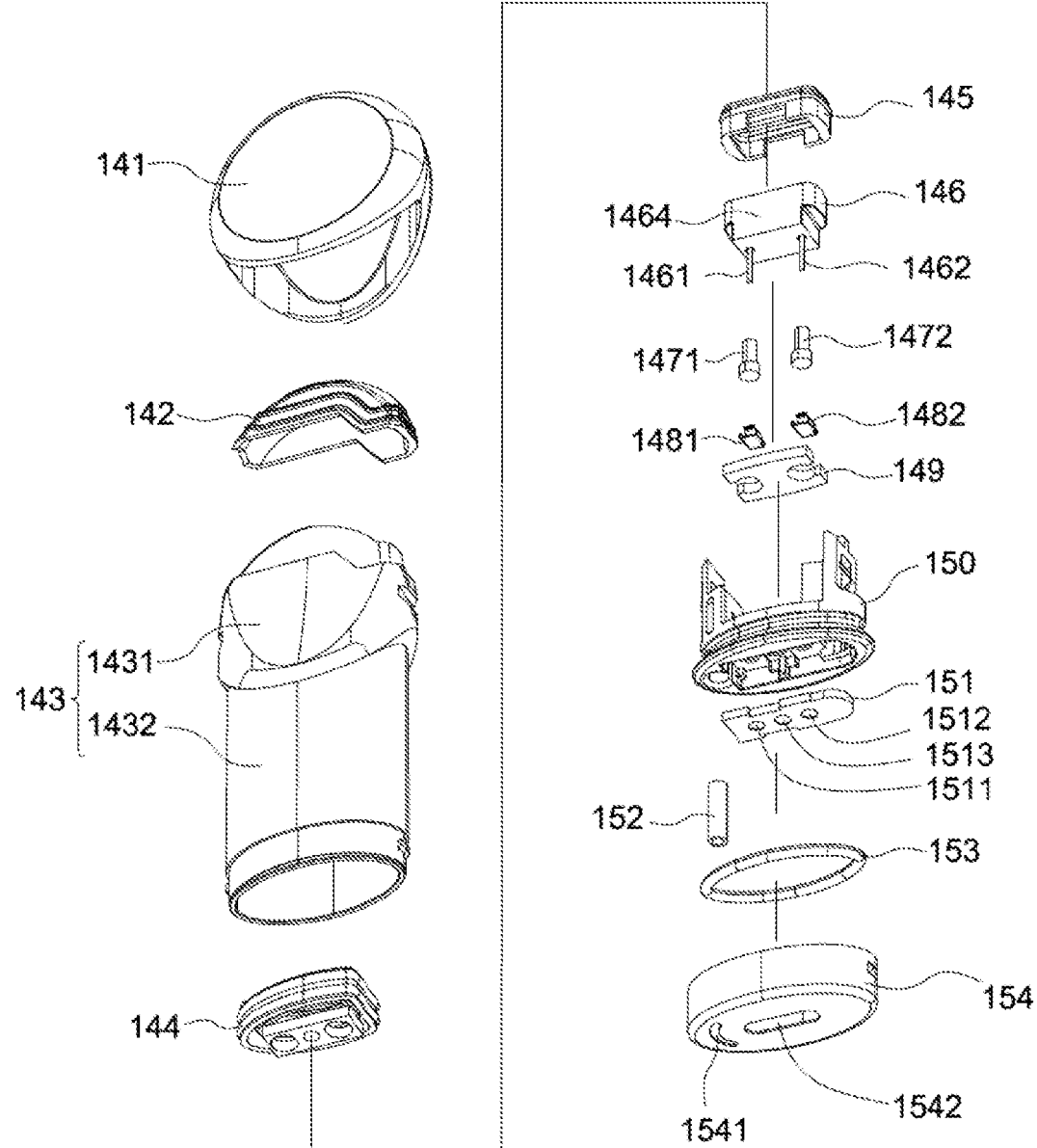
FIG. 16 is a schematic diagram of a disassembly structure of a cartridge according to some embodiments of the present application.

FIG. 14 and FIG. 16 are schematic diagrams of disassembly structures of the cartridge 11 according to some embodiments of the present application. The cartridge 11 includes a heating component 146, a pin 1471, a pin 1472, an elastic piece 1481, an elastic piece 1482, and a printed circuit board (PCB) module 151. In some embodiments, the heating component 146, the pin 1471, the pin 1472, the elastic piece 1481, the elastic piece 1482, and the PCB module 151 constitute the heating circuit 111 in some embodiments of the present application. In some embodiments, the heating component 146, the pin 1471, the pin 1472, the elastic piece 1481, the elastic piece 1482, and the PCB module 151 constitute the heating circuit 111 and the authentication circuit 112 in some embodiments of the present application, where a resistor (not shown in the figure) indicating flavor information of the cartridge 11 is disposed on the PCB module 151. In some embodiments, the encryption chip (not shown in the figure) in the foregoing embodiment is further disposed on the PCB module 151.

Figure 15:
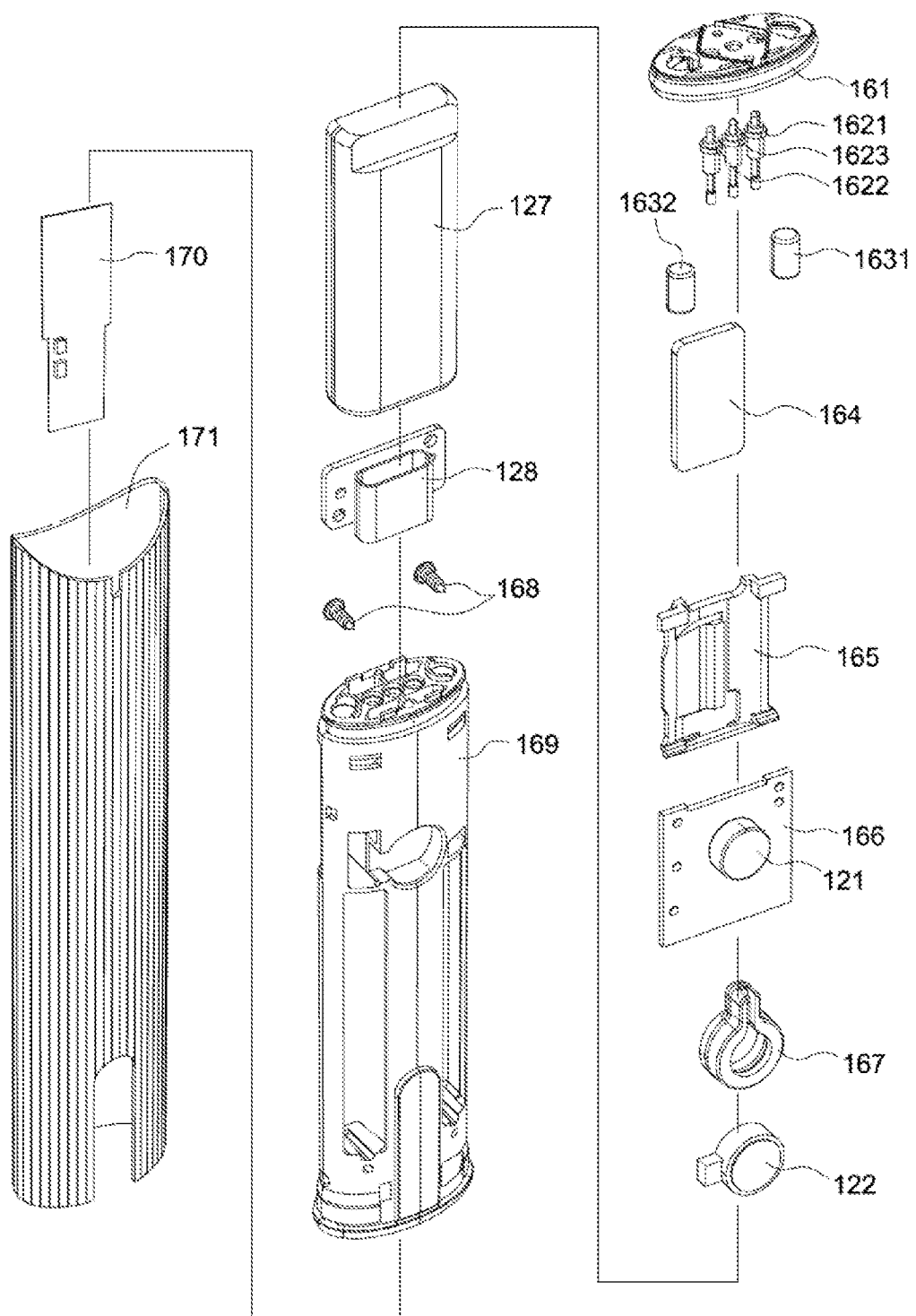
FIG. 15 is a schematic diagram of a disassembly structure of a cigarette rod according to some embodiments of the present application.
Figure 17:
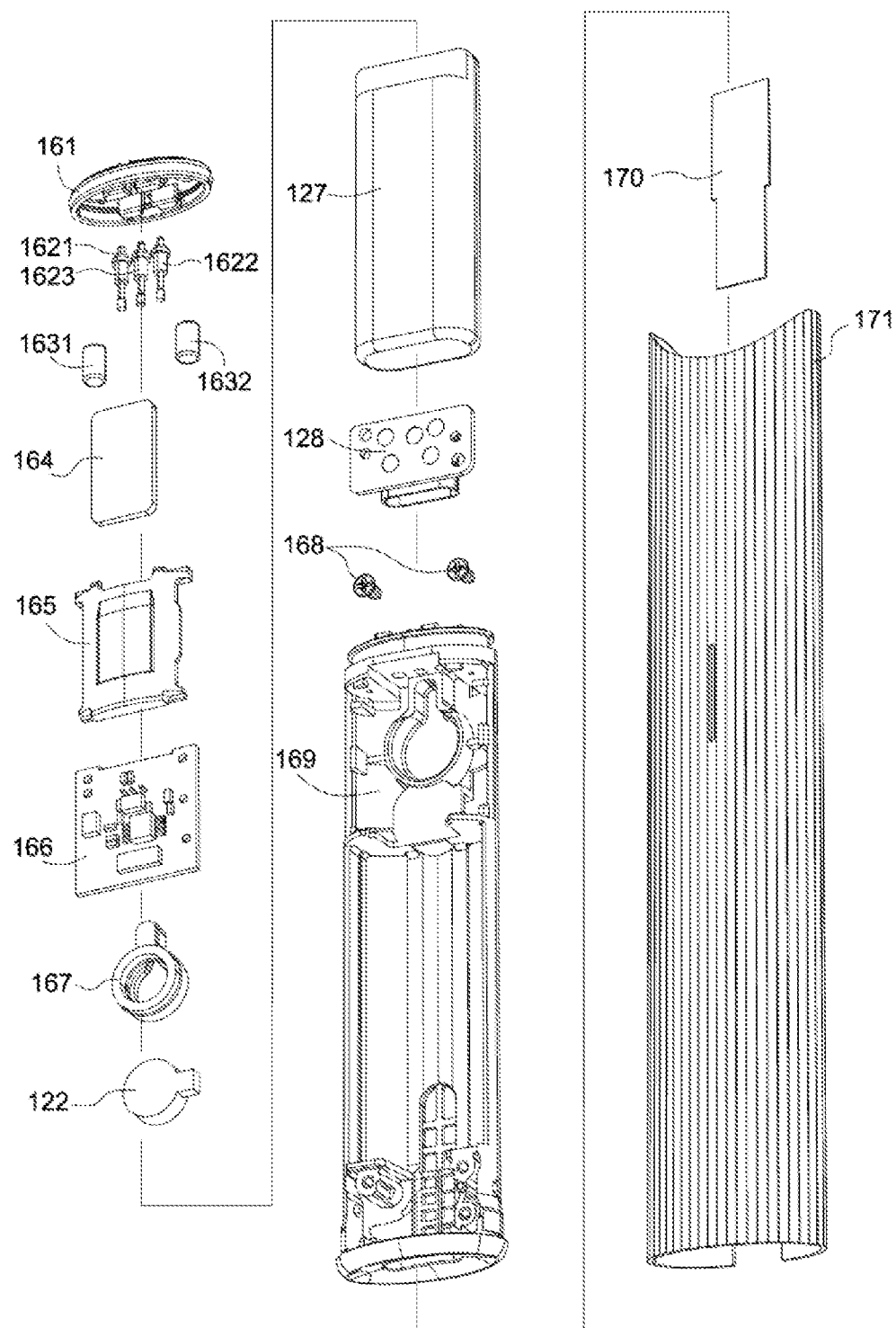
FIG. 17 is a schematic diagram of a disassembly structure of a cigarette rod according to some embodiments of the present application.

FIG. 15 and FIG. 17 are schematic diagrams of disassembly structures of the cigarette rod 12 according to some embodiments of the present application. The cigarette rod 12 includes a pogo pin 1621, a pogo pin 1622, a pogo pin 1623, a main control module 166, a motor 122, a battery 127, a charging module 128, and an antenna 170. The main control module 166 and the antenna 170 consist of the main control circuit 123, the memory 124, the wireless communication circuit 125, and the indicator light 126 in some embodiments of the present application. In some embodiments of the present application, the pogo pin 1621, the pogo pin 1622, and the pogo pin 1623 are all used as pins for electrical connection, or may be referred to as a pin 1621, a pin 1622, and a pin 1623. In some embodiments, the pogo pin 1621 and the pogo pin 1622 may be used as pins for external power supply, and the pogo pin 1623 may be used as a pin for external data.

The disassembled cartridge 11 in FIG. 14 and the disassembled cigarette rod 12 in FIG. 15 may form the electronic cigarette 10 as shown in FIG. 2B after being installed and assembled. The disassembled cartridge 11 in FIG. 16 and the disassembled cigarette rod 12 in FIG. 17 may form the electronic cigarette 10 as shown in FIG. 2B after being installed and assembled.

Figure 18:
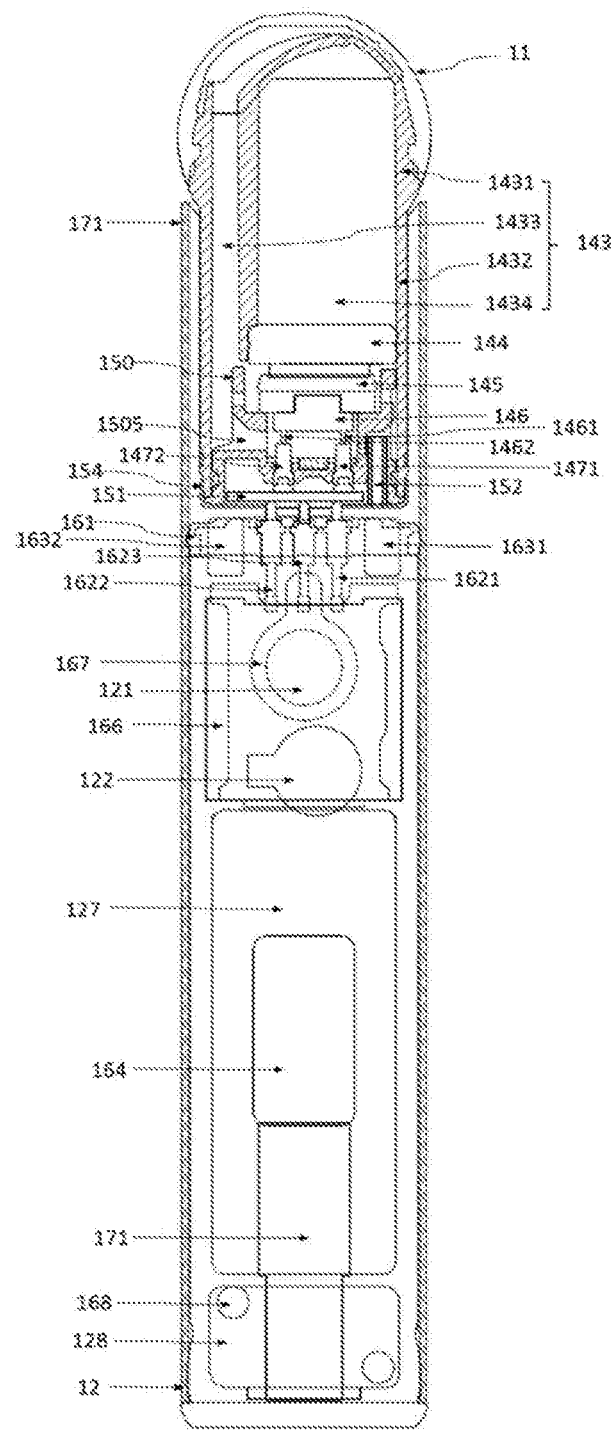
FIG. 18 is a schematic structural diagram of a partial section of an electronic cigarette according to some embodiments of the present application.

FIG. 18 is a schematic structural diagram of a partial section of the electronic cigarette according to some embodiments of the present application. The cartridge 11 is inserted into the cigarette rod 12, the cartridge 11 and the cigarette rod 12 being in the engaged state, as shown in FIG. 2B. The heating component 146 includes the pin 1461 and the pin 1462. The pin 1461, the pin 1471, and the elastic piece 1481 are electrically connected to the pogo pin 1621 through a PCB module 151, and the pin 1462, a pin 1472, and the elastic piece 1482 are electrically connected to the pogo pin 1622 via the PCB module 151, as shown in FIGS. 14-17. The pogo pin 1621, the pogo pin 1622, and the pogo pin 1623 are all electrically connected to the main control module 166. When the cartridge 11 is not engaged with the cigarette rod 12, as shown in FIG. 2A, the pogo pin 1621, the pogo in 1622, and the pogo pin 1623 are not in contact with the PCB module 151. The pin 1461, the pin 1462, the pin 1471, the pin 1472, the elastic piece 1481, the elastic piece 1482, the pogo pin 1621, and the pogo pin 1622 are all made of a conductive material. In some embodiments, the pin 1462 and the pin 1462 may be used as a positive pole and a negative pole respectively. In some embodiments, the pin 1462 and the pin 1462 may be used as a negative pole and a positive pole respectively.

The cartridge 11 further includes a tube body 143, a heating base 150, and a bottom cap 154. The tube body 143 includes an upper tube body 1431 and a lower tube body 1432. The bottom cap 154 is disposed at the bottom of the tube body 1432 and is fixed to the tube body 1432 through a locking structure. The upper tube body 1431 is an upper portion of the tube body 143, and the lower tube body 1432 is a lower portion of the tube body 143. The heating base 150 is disposed within the lower tube body 1432 and located on the bottom cap 154. The PCB module 151 is disposed within the lower tube body 1432, and located between the heating base 150 and the bottom cap 154. The elastic piece 1481 and the elastic piece 1482, the pin 1471 and the pin 1472, and the heating component 146 are successively disposed in the heating base 150, and the elastic piece 1481 and the elastic piece 1482 are in electrical contact with two contact pads of an upper end portion of the PCB module 151. The two contact pads at the upper end portion of the PCB module 151 are electrically connected to a contact pad 1511 and a contact pad 1512 at the lower end portion through circuits or leads inside the PCB module 151 respectively. The pin 1471 and the pin 1472 pass through a through hole 1501 and a through hole 1502 at the bottom of the heating base 150 and are in contact with the elastic piece 1481 and the elastic piece 1482 respectively. The pin 1461 and the pin 1462 of the heating component 146 are respectively received within cavities of the pin 1471 and the pin 1472, and may be in electrical contact with the pin 1471 and the pin 1472. In some embodiments of the present application, the pin 1471 and the pin 1472 have a pin tube and a pin base. The pin tube of the pin 1471 is configured to receive or contain the pin 1461 and is in electrical contact with the pin 1461, the pin tube of the pin 1472 is configured to receive or contain the pin 1462 and is in electrical contact with the pin 1462, and the pin base of the pin 1471 and the pin base of the pin 1472 are respectively in electrical contact with two contact pads at the upper end portion of the PCB module 151.

Figure 19:
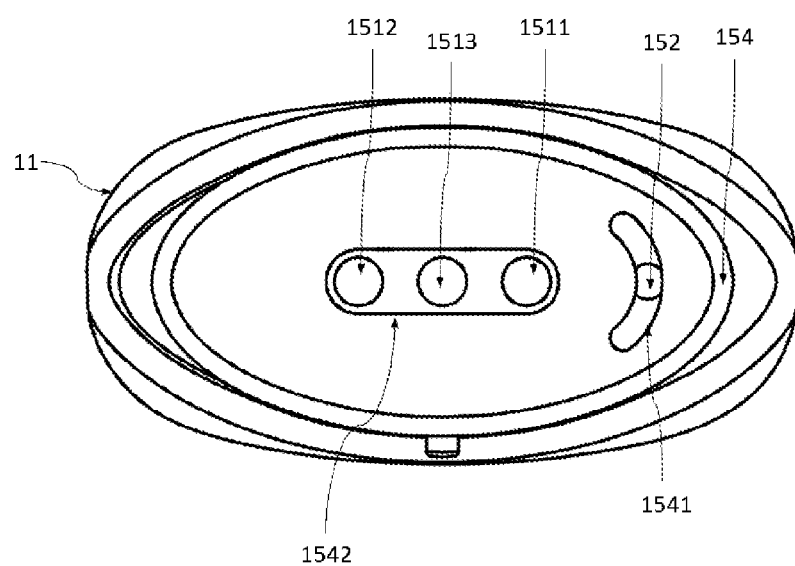
FIG. 19 is a schematic bottom view of a cartridge according to some embodiments of the present application.

FIG. 19 is a schematic structural bottom view of the cartridge 11 according to some embodiments of the present application. As shown in FIG. 19, the lower end portion of the PCB module 151 further includes a contact pad 1511, a contact pad 1512, and a contact pad 1513. The contact pad 1511, the contact pad 1512, and the contact pad 1513 are located in the through hole 1541 of the bottom cap 154, so that the contact pad 1511, the contact pad 1512, and the contact pad 1513 are respectively in electrical contact with the pogo pin 1621, the pogo pin 1622, and the pogo pin 1623 when the cartridge 11 is engaged with the cigarette rod 12. In some embodiments, the contact pad 1511, the contact pad 1512, and the contact pad 1513 are integrated in the PCB module 151. In some embodiments, after the cartridge 11 is in contact with the pogo pin of the cigarette rod through the contact pad, because the cartridge itself has resistance, a change in a voltage or a current is generated between the pogo pin 1621 and the pogo pin 1622, that is, the main control module 166 detects an output level value of a connection circuit in which the pogo pin 1621 and the pogo pin 1622 are located. For example, in some embodiments, when the electrical contact occurs, the output level value is a high level value. In some embodiments, when the electrical contact occurs, the output level value is a low level value.

In some embodiments of the present application, the cartridge 11 further includes a tar absorbing pad 149. The tar absorbing pad 149 may be configured to absorb e-liquid that may leak. The material of the e-liquid absorbing pad 149 is cotton, which may be selected according to practical conditions, and is not limited thereto. Both sides of the tar absorbing pad 149 are provided with through holes or openings, and the through holes or openings may wrap outer walls of upper half portions of the pin 1471 and the pin 1472.

Figure 20A:
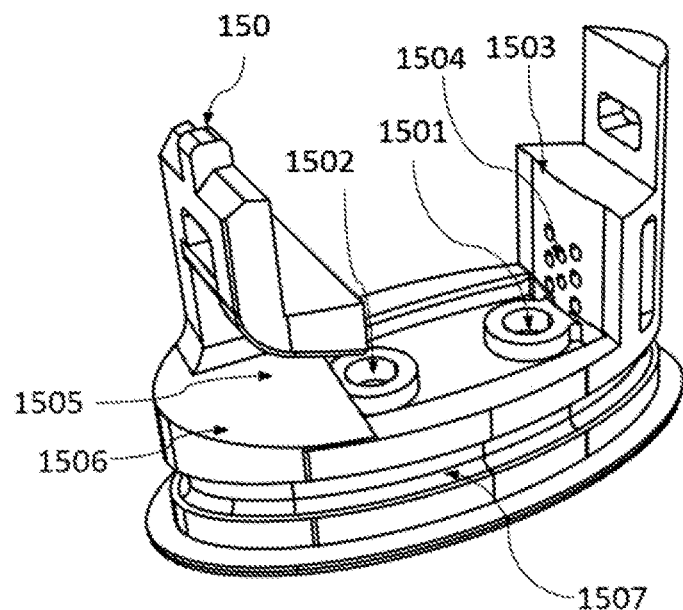
FIGS. 20A-20B are schematic structural diagrams of a heating base according to some embodiments of the present application.
Figure 20B:
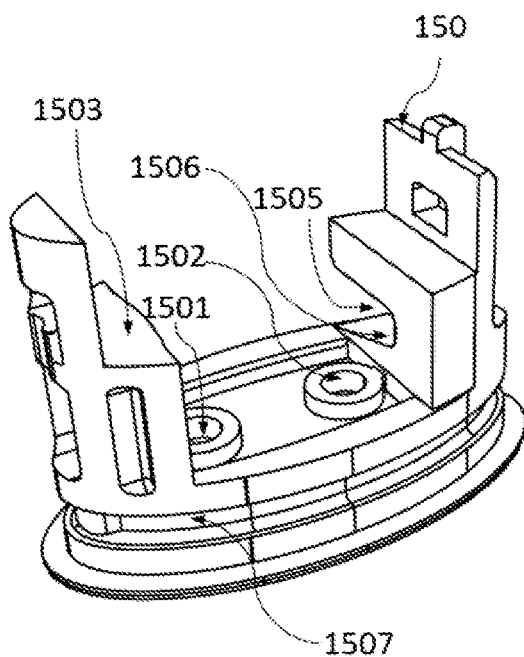

FIGS. 20A-20B are schematic structural diagrams of the heating base 150 according to some embodiments of the present application. The heating base 150 includes a base body (not shown), a first side end structure, and a second side end structure. A through hole 1501 and a through hole 1502 are disposed on the base body. The first side end structure and the second side end structure are respectively located at opposite two sides of the base. The heating base 150 includes a side end cavity 1503, one or more through holes 1504, and a side end opening 1505. The side end cavity 1503 is disposed in the first side end structure, and the side end opening 1505 is disposed in the second side end structure. One or more through holes 1504 are disposed in the side end cavity 1503 and are close to a side of the side end opening 1505. The side end opening 1505 communicates the space in an air outlet channel 1433 of a tube body 143 with the space between the heating body 1464 and the tar absorbing pad 149 to be used as a part of the channel for the communication of smoke and airflow in the cartridge 11.

In some embodiments of the present application, the cartridge 11 further includes an air tube 152. The air tube 152 is disposed between the heating base 150 and a bottom cap 154, and an upper end opening of the air tube 152 is located in the side end cavity 1503 of the heating base 150. The through hole 1504 communicates the space of the upper end opening of the air tube 152 with the space inside the heating base 150. The lower end opening of the air tube 152 is disposed in the bottom cap 154, is exposed by a through hole 1541, and is slightly lower than an outer surface of the bottom cap 154, or is flush with the outer surface of the bottom cap 154. The lower end opening of the air tube 152 is in communication with the space outside the cartridge 11. In some embodiments of the present application, the heating base 150 further includes a ramp structure 1506. The ramp structure 1506 is located at the bottom of the heating base 150 and becomes a part of the side end opening 1505. The ramp structure 1506 can prevent the e-liquid from entering an airflow channel 1433 on the left side of the tube body 143 when a user is vaping or inhaling.

In some embodiments of the present application, a height of the opening 1504 from the bottom cap 154 is greater than a height of the tar absorbing pad 149 from the bottom cap 154, so that the tar is first absorbed by the tar absorbing pad 149 if leaking and does not leak to the outside of the cartridge 11 through the air tube 152, thereby improving user experience. In some embodiments, a height of the upper end opening of the airflow tube 152 from the bottom cap 154 is greater than heights of several through holes 1504 from the bottom cap 154, so that the e-liquid can flow out of the through hole 1504 and is still saved in the cartridge 11 even if the e-liquid in the cartridge 11 leaks and when the e-liquid overflows to the through hole 1504, and the e-liquid does not overflow to the outside the cartridge 11 through the upper end opening of the air tube 152, thereby improving user experience. In some embodiments, the material of the air tube 152 is steel, but is not limited thereto.

In some embodiments of the present application, the cartridge 11 further includes an O-ring 153. The O-ring 153 is disposed around an outer side wall of the heating base 150. In some embodiments of the present application, an outer wall of the base body of the heating base 150 is provided with a groove, the groove being an annular groove 1507, as shown in FIG. 20A and FIG. 20B. The O-ring 153 is nested in the annular groove 1507 for sealing the outer wall of the heating base 153 and an inner wall of the tube body 143 to prevent the e-liquid from leaking out of the cartridge 11.

In some embodiments of the present application, the cartridge 11 further includes a heat-conducting top cap 144 and a heat-conducting silica gel 145. The tube body 143 further includes a storage compartment 1434. Both the heat-conducting top cap 144 and the heat-conducting silica gel 145 have several through holes (not shown in the figure), and the e-liquid stored in the storage compartment 1434 is in contact with the heating component 146 via permeating through the through holes in the heat-conducting top cap 144 and the through holes in the heat-conducting silica gel 145. When the heating component 146 is energized or powered for heating, a temperature generated by the heating component 146 will vaporize the e-liquid that is in contact with the heating component 146. The through holes of the heat-conducting top cap 144 and a shape, a size and a number of the heat-conducting silica gel 145 are adjusted according to viscosity of the e-liquid, so that the heating component 146 can be effectively in contact with the e-liquid, to avoid dry burning and causing a burnt odor.

Figure 21A:
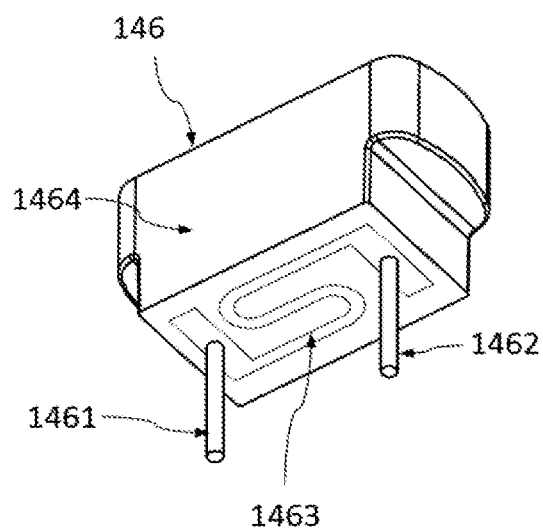
FIGS. 21A-21C are schematic structural diagrams of a heating component according to some embodiments of the present application.
Figure 21B:
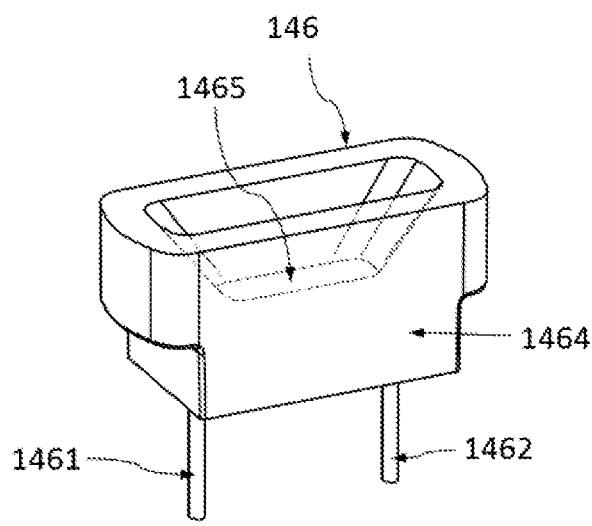
Figure 21C:
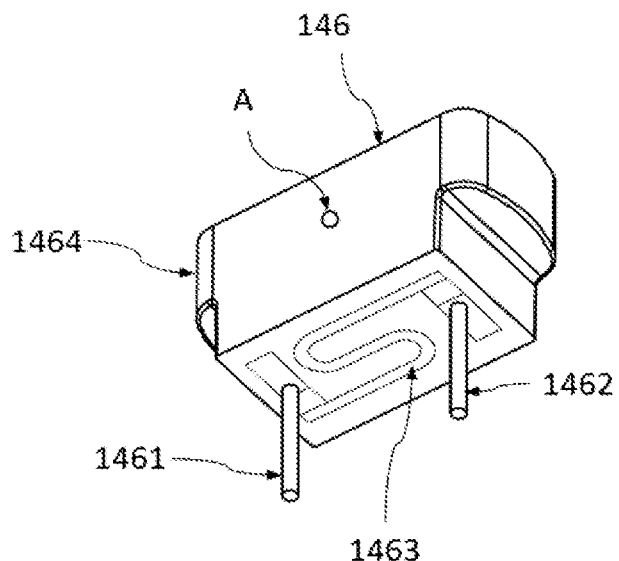

FIGS. 21A-21C are schematic structural diagrams of a heating component according to some embodiments of the present application. A heating component 146 includes a pin 1461, a pin 1462, a heating element 1463, and a heating body 1464. The pin 1461, the pin 1462, and the heating element 1463 are all disposed in the heating body 1464. In some embodiments, the heating element 1463 may be printed on the bottom surface of the heating body 1464 via circuit printing technology. The heating body 1464 is further provided with a groove 1465. As described above, the e-liquid in the storage compartment 1434 penetrates into the surface of the groove 1465 in the heating component 146 through the through holes in the heat-conducting top cap 144 and the heat-conducting silica gel 145, to be in contact with the heating body 1464. The pin 1461, the heating element 1463, and the pin 1462 are electrically connected in sequence. When the pin 1461 and the pin 1462 are powered, the heating element 1463 generates heat to raise the temperature of the heating body 1464, and after the temperature rises above a critical value of e-liquid vaporization, the e-liquid that is in contact with the heating body 1464 is vaporized.

In some embodiments of the present application, the heating element 1463 may be printed on an interior of the heating body 1464 via circuit printing technology. In this way, the heating element 1463 may be prevented from being damaged during subsequent assembly. The heating element 1463 may include metallic materials. In some embodiments, the heating element 1463 may include silver. In some embodiments, the heating element 1463 may include platinum. In some embodiments, the heating element 1463 may include palladium. In some embodiments, the heating element 1463 may include a nickel alloy material. The material included in the heating element 1463 is not limited to the foregoing, and may be selected according to practical conditions.

In some embodiments of the present application, the heating element 1463 may be printed on a bottom surface of the groove 1465 in the heating body 1464 via circuit printing technology.

In some embodiments of the present application, the heating body 1464 may include a ceramic material and a diatomaceous earth material. The heating body 1464 may include aluminium oxide. In some embodiments, the heating body 1464 may include a semiconductor ceramic material. In some embodiments, the heating body 1464 may include a heavily doped silicon carbide. In some embodiments, the heating body 1464 may include barium titanate. In some embodiments, the heating element 1464 may include strontium titanate. The material included in the heating body 1464 is not limited to the foregoing, and may be selected according to practical conditions.

The heating body 1464 may have a temperature self-limiting characteristic. A resistance value of the heating body 1464 may be increased as the temperature rises. When the temperature of the heating body 1464 reaches a critical value CV1, the heating body 1464 has a resistance value R1. In some embodiments, when the temperature of the heating body 1464 reaches a critical value CV1, the heating element 1463 can no longer raise the temperature of the heating body 1464. In some embodiments, when the resistance value of the heating body 1464 reaches R1, heating power output by the heating element 1463 can no longer raise the temperature of the heating body 1464.

In some embodiments of the present application, the critical value CV1 is in the range of 200° C. to 220° C. In some embodiments, the critical value CV1 is in the range of 220° C. to 240° C. In some embodiments, the critical value CV1 is in the range of 240° C. to 260° C. In some embodiments, the critical value CV1 is in the range of 260° C. to 280° C. In some embodiments, the critical value CV1 is in the range of 280° C. to 300° C. In some embodiments, the critical value CV1 is in the range of 280° C. to 300° C. In some embodiments, the critical value CV1 is in the range of 300° C. to 320° C. A specific range of the critical value CV1 is limited by the material included in the heating body 1464, and the material included in the heating body 1464 and the required critical value CV1 may be selected according to practical conditions.

In some embodiments of the present application, the heating body 1464 has a resistance value greater than 10Ω when being heated to the critical value CV1. In some embodiments, the heating body 1464 has a resistance value greater than 15Ω when being heated to the critical value CV1. In some embodiments, the heating body 1464 has a resistance value greater than 20Ω when being heated to the critical value CV1. In some embodiments, the heating body 1464 has a resistance value greater than 30Ω when being heated to the critical value CV1.

The temperature self-limiting characteristic of the heating body 1464 can prevent the heating component 146 from dry burning and enable the heating component 146 to continuously heat up when the heating component 146 is energized. The temperature self-limiting characteristic of the heating body 1464 may reduce a probability of burning the electronic cigarette 10. The temperature self-limiting characteristic of the heating body 1464 may increase the safety of the electronic cigarette 10. The temperature self-limiting characteristic of the heating body 1464 may prolong the service life of the electronic cigarette 10.

Figure 21D:
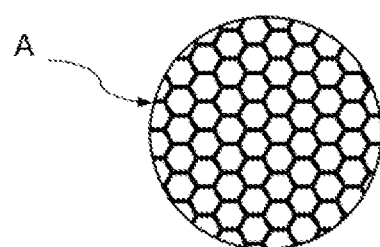
FIG. 21D is an enlarged schematic structural diagram of a body of a heating component at A according to some embodiments of the present application.

As shown in FIG. 21C, the heating body 1464 may have one or more pores. In some embodiments, a shape of the pore may be in the shape of a square. In some embodiments, a shape of the pore may be a cylinder. In some embodiments, a shape of the pore may be a ring. In some embodiments, a shape of the pore may be a hexagonal cylinder. FIG. 21D is an enlarged schematic structural diagram of the heating body 1464 at A. In some embodiments, a shape of the pore may be presented as a honeycomb structure.

The e-liquid may penetrate into the pores of the heating body 1464. The pores of the heating body 1464 may be infiltrated in the e-liquid. The pores of the heating body 1464 may increase a contact area between the heating body 1464 and the e-liquid. The pores of the heating body 1464 may surround small molecules of the e-liquid from all sides. During heating, the pores of the body 1464 may allow the e-liquid to be more evenly heated. During heating, the pores of the body 1464 may allow the e-liquid to reach a predetermined temperature faster. During heating, the pores of the body 1464 may prevent a burnt odor from being generated.

In some embodiments, the heating body 1464 has a porosity of 20% to 30%. In some embodiments, the heating body 1464 has a porosity of 30% to 40%. In some embodiments, the heating element 1464 has a porosity of 40% to 50%. In some embodiments, the heating body 1464 has a porosity of 50% to 60%. In some embodiments, the heating body 1464 has a porosity of 60% to 70%. In some embodiments, the heating body 1464 has a porosity of 70% to 80%.

Figure 22:
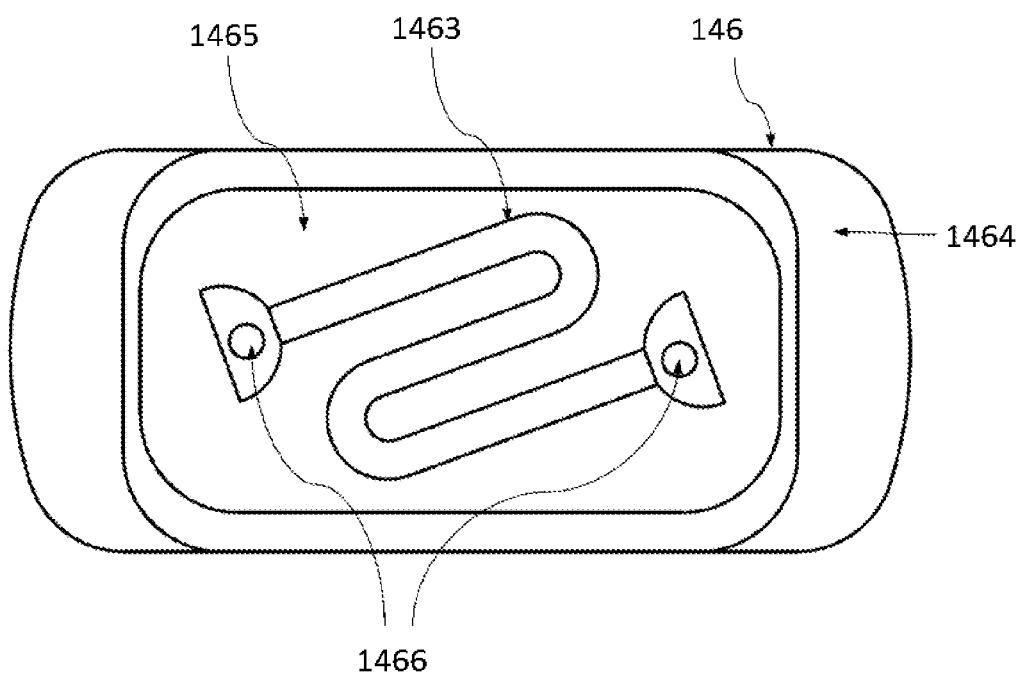
FIG. 22 is a schematic structural diagram of a heating component according to some embodiments of the present application.

FIG. 22 is a schematic structural diagram of the heating component according to some embodiments of the present application. The heating component 146 further includes a protection element 1466. The protection element 1466 is disposed in the heating body 1464 and is coupled between the pin 1461, the heating element 1463, and the pin 1462 to form a series circuit. The protection element 1466 is resettable. In some embodiments, the protection element 1466 is a resettable fuse. The protection element 1466 may be disposed at either end or both ends of the heating element 1463. The protection element 1466 may be integrally formed through high sintering during the process of fabricating the heating component 146.

When the temperature of the protection element 1466 rises to a critical value CV2, the protection element 1466 forms an open circuit, so that the series circuit formed by the pin 1461, the heating element 1463, the protection element 1466, and the pin 1462 forms an open circuit, that is, the heating element 1463 no longer performs heating. When a temperature of the protection element 1466 falls to a critical value CV3, the protection element 1466 forms a short circuit, so that the series circuit formed by the pin 1461, the heating element 1463, the protection element 1466, and the pin 1462 forms a switch-on circuit, that is, the heating element 1463 performs heating.

In some embodiments, the critical value CV3 may be the same as the critical value CV2. In some embodiments, the critical value CV3 may be different from the critical value CV2. In some embodiments, the critical value CV3 is less than the critical value CV2.

In some embodiments, the critical value CV2 is in the range of 200° C. to 220° C. In some embodiments, the critical value CV2 is in the range of 220° C. to 240°. In some embodiments, the critical value CV2 is in the range of 240° C. to 260° C. In some embodiments, the critical value CV2 is in the range of 260° C. to 280° C. In some embodiments, the critical value CV2 is in the range of 280° C. to 300° C. In some embodiments, the critical value CV2 is in the range of 300° C. to 320° C.

In some embodiments, the critical value CV3 is in the range of 180° C. to 200° C. In some embodiments, the critical value CV3 is in the range of 200° C. to 220° C. In some embodiments, the critical value CV3 is in the range of 220° C. to 240° C. In some embodiments, the critical value CV3 is in the range of 240° C. to 260° C. In some embodiments, the critical value CV3 is in the range of 260° C. to 280° C. In some embodiments, the critical value CV3 is in the range of 280° C. to 300° C.

In some embodiments of the present application, the protection element 1466 is non-resettable, for example, is a non-resettable fuse. When the temperature of the protection element 1466 rises to a critical value CV4, the protection element 1466 forms an open circuit. In some embodiments, the protection element 1466 forming the open circuit may not form a short circuit due to a temperature drop.

The protection element 1466 may prevent the heating element 1465 from dry burning. The protection element 1466 may reduce a probability of burning the electronic cigarette 10. The protection element 1466 may increase the safety of the electronic cigarette 10. The protection element 1466 may prolong the service life of the electronic cigarette 10.

In some embodiments of the present application, the cartridge 11 further includes a mouthpiece cap 141 and a vaping cap 142. The vaping cap 142 covers on a portion of the upper tube body 1431. When the user is vaping via the electronic cigarette 10, the vaping cap 142 is in contact with the user's mouth. The material of the vaping cap 142 is silica gel, but is not limited thereto. The mouthpiece cap 141 wraps an entire vaping cap 142 and is sleeved on most of the portion of the upper tube body 1431. Through holes for venting are disposed on both the upper tube body 1431 and the vaping cap 142. Locations of the through holes are substantially corresponding to each other to be capable of feeding the vapor of the e-liquid to the user's mouth.

In some embodiments of the present application, the cigarette rod 12 includes a battery holder cap 161, a housing 171, and a battery holder 169. The battery holder 169 is mounted in the housing 171. The battery holder cap 161 is mounted on an upper end portion of the battery holder 169 to form an accommodating space at the upper end of the battery holder cap 161 in the housing 171. The accommodating space is configured to accommodate a lower tube body 1432 of the cartridge 11, and the upper tube body 1431 of the cartridge 11 is located outside the housing 171. In some embodiments of the present application, a structure at a junction between the upper tube body 1431 and the lower tube body 1432 matches a structure at the upper end portion of the housing 171. The upper end portion of the battery holder 169 has a through hole for accommodating the pogo pin 1621, the pogo pin 1622, and the pogo pin 1623, and a through hole for ventilation. The cigarette rod 12 further includes a magnet 1631 and a magnet 1632. The upper end portion of the battery holder 169 is further provided with a through hole for mounting the magnet 1631 and the magnet 1632. The pogo pin 1621, the pogo pin 1622, and the pogo pin 1623 are located between the magnet 1631 and the magnet 1632.

Figure 23:
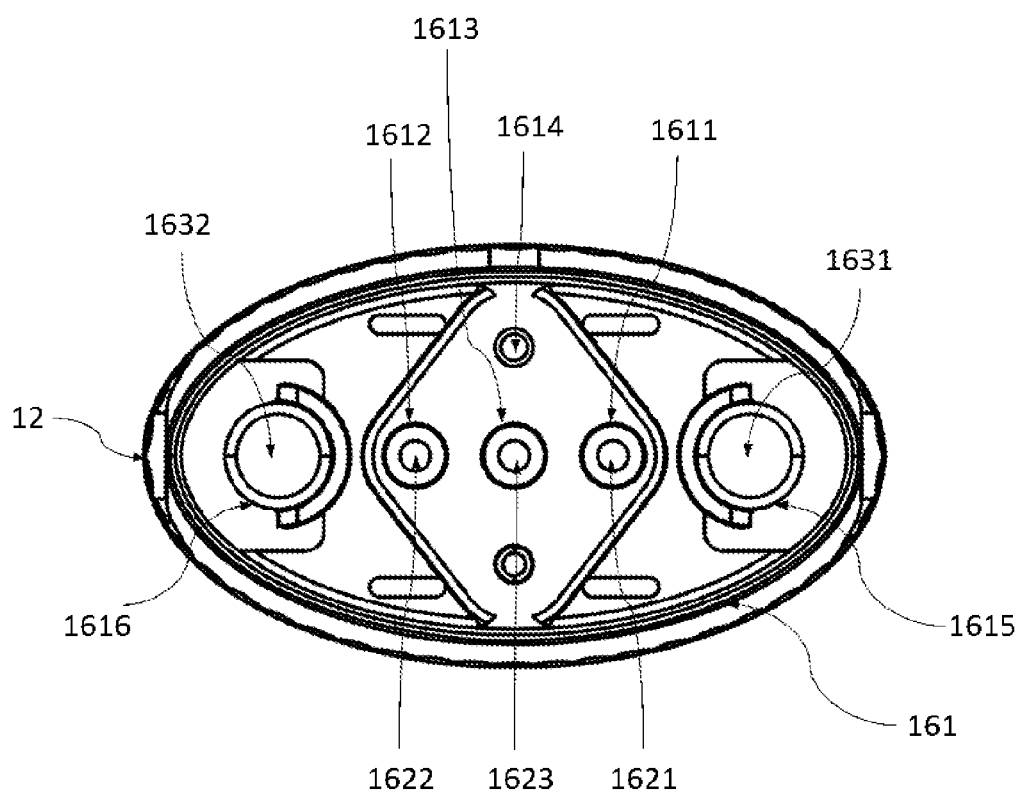
FIG. 23 is a schematic structural top view of a cigarette rod according to some embodiments of the present application.

FIG. 23 is a schematic structural top view of the cigarette rod 12 according to some embodiments of the present application. There is a structure corresponding to an upper end portion of a battery holder 169 in a battery holder cap 161. As shown in FIG. 23, a through hole 1611, a through hole 1612, a through hole 1613, a through hole 1614, a through hole 1615, and a through hole 1616 are disposed on the battery holder cap 161. The pogo pin 1621, the pogo pin 1622, and the pogo pin 1623 extend from the through hole 1611, the through hole 1612, and the through hole 1613, respectively. The magnet 1631 and the magnet 1632 are located in the through hole 1615 and the through hole 1616, respectively. In some embodiments, the top ends of the magnet 1631 and the magnet 1632 are flush with a cap face of the battery holder cap 161. In some embodiments, the top ends of the magnet 1631 and the magnet 1632 are slightly lower than a cap face of the battery holder cap 161. In some embodiments, the top ends of the magnet 1631 and the magnet 1632 are slightly higher than a cap face of the battery holder cap 161. The magnet 1631 and the magnet 1632 are configured to attract the cartridge 11 and the cigarette rod 12 through a magnetic force when the cartridge 11 and the cigarette rod 12 are engaged, so that the cartridge 11 or the cigarette rod 12 can be prevented from sliding when the user vapes via the electronic cigarette 10, thereby improving user experience. In addition, the through hole 1614 is configured to communicate an airflow detection mouth or hole of an airflow sensor 121 inside the cigarette rod 12 with external space.

After the battery holder cover 161 covers an upper end portion of the battery holder 169, the pogo pin 1621, the pogo pin 1622, and the pogo pin 1623 may be in contact with the contact pad 1511, the contact pad 1512, and the contact pad 1513 respectively at the lower end portion of the PCB module 151 in the cartridge 11, so that the pogo pin 1621, the pogo pin 1622, and the pogo pin 1623 are all electrically connected to a main control module 166. The main control module 166, the battery 127, the charging circuit 128, the motor 122, and the airflow sensor 121 are all installed in a corresponding structure in the battery holder 169, and the battery 127, the charging circuit 128, the motor 122, and the airflow sensor 121 are all electrically connected to the main control module 166.

In some embodiments of the present application, the cigarette rod 12 further includes a silicone sleeve 167. The silicone sleeve 167 is configured to protect the airflow sensor 121. The cigarette rod 12 further includes a light guide bar holder 165. The light guide bar holder 165 is disposed on the battery holder 169 and is located at one side of the main control module 166. An indicator light 126 is disposed on the main control module 166 and is located between the main control module 166 and the light guide bar holder 165. When the indicator light 124 is on, light information may be displayed to the user through the light guide bar holder 165 and the through hole in a housing 171.

In some embodiments of the present application, the battery 128 is located between the main control module 166 and the charging circuit 128. The charging circuit 128 is fixed to the battery holder 169 using screws 168. The cigarette rod 12 further includes the antenna 170 for receiving and transmitting the wireless signal. The antenna 170 is disposed between one side of the battery 127 and the housing 171, and the antenna 170 is electrically connected to the main control module 166. In some embodiments of the present application, the cigarette rod 12 further includes a sponge pad 164, the sponge pad 164 is disposed between the other side of the battery 127 opposite the antenna 170 and the housing 171. The sponge pad 164 is in contact with the battery 127 and an inner wall of the housing 171 to provide a cushioning force. When the cartridge 11 is engaged with the cigarette rod 12, the accommodating space in the housing 171 accommodates a lower tube 1432 and a bottom cap 154 in the cartridge 11.

In some embodiments of the present application, when the cartridge 11 is not engaged with the cigarette rod 12, the through hole 1614 for ventilation of the battery holder cap 161 in the cigarette rod 12 may enable outside air to be in communication with the airflow detection through hole of the airflow sensor 121.

Figure 24:
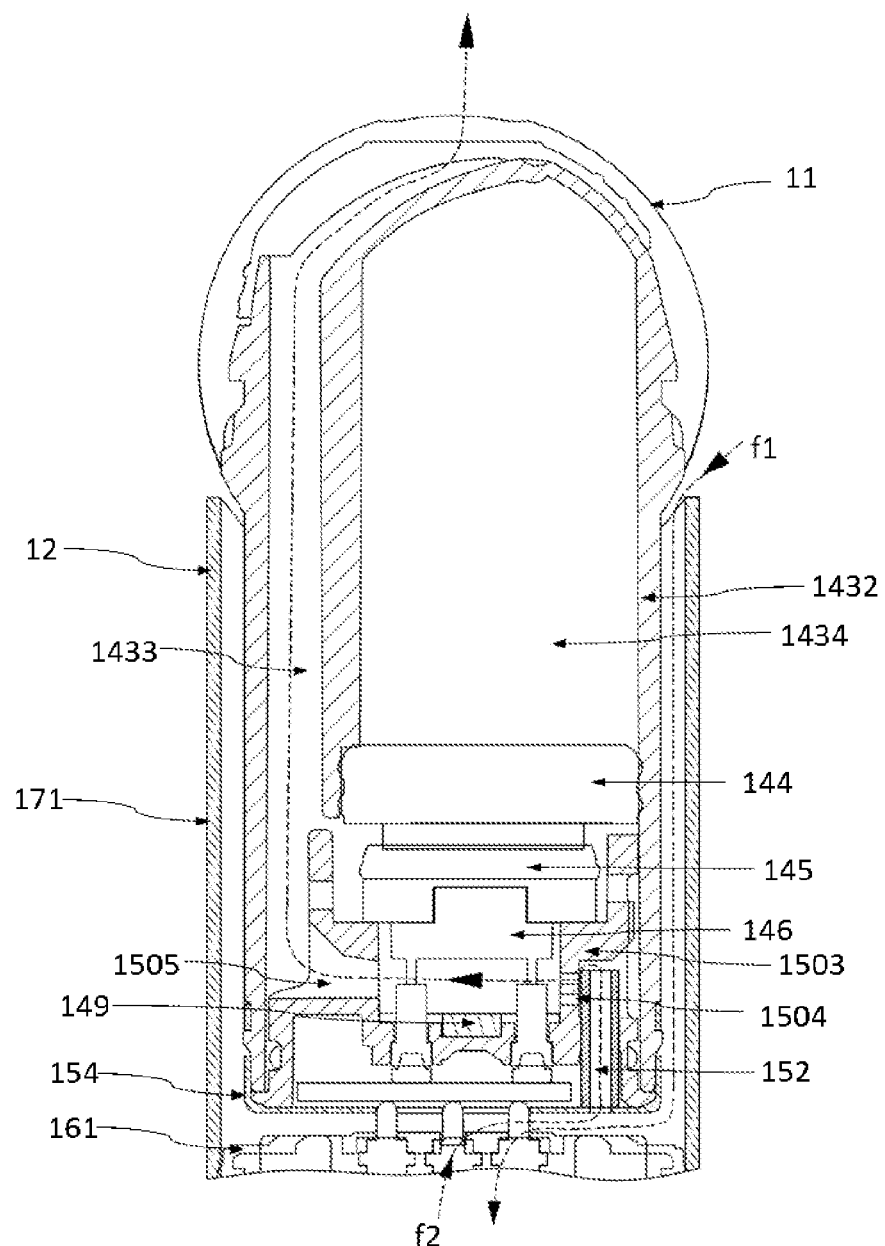
FIG. 24 is a schematic structural diagram of an airflow channel of an electronic cigarette according to some embodiments of the present application.
Figure 25:
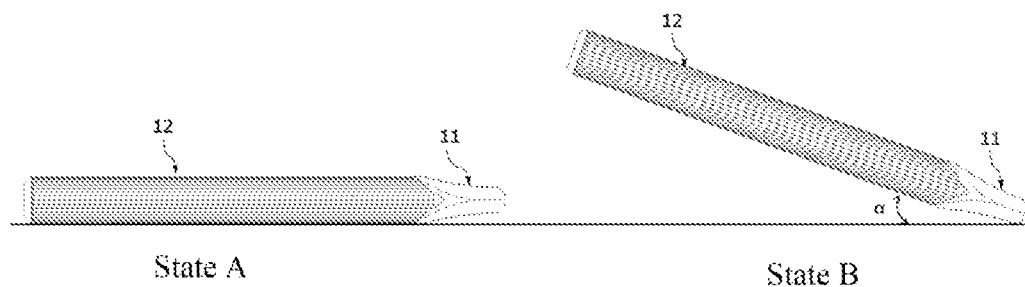
FIG. 25 is a schematic diagram of an electronic cigarette in different states according to some embodiments of the present application.

FIG. 24 is a schematic structural diagram of an airflow channel of the electronic cigarette 10 according to some embodiments of the present application. As shown in FIG. 24, when the cartridge 11 is engaged with the cigarette rod 12, there is a gap between an outer side wall of a lower tube body 1432 of the cartridge 11 and an inner side wall of a housing 171 of the cigarette rod 12, and there is also a gap for ventilation between a bottom cap 154 of the cartridge 11 and a battery holder cap 161 of the cigarette rod 12. The airflow enters an airflow detection through hole of an airflow sensor 121 through the through hole 1614 for air circulation of the battery holder cap 161, to form an airflow channel f1 for communicating outside air of the electronic cigarette 10 with the airflow sensor 121 of the electronic cigarette. In this way, the outside air of the electronic cigarette 10 can effectively enter.

When the cartridge 11 of the electronic cigarette 10 is engaged with the cigarette rod 12, when the user performs a vaping action, the airflow at the airflow detection through hole of the airflow sensor 121 passes through the through hole 1614 at the battery holder cap 161 to enter the gap between the bottom cap 154 and the battery holder cap 161, that is, the air flow is detected, the air flow changes, and a high level is output. A main control module 166 enables the battery 12 to supply power to the heating component 146, and the heating component 146 heats the e-liquid. Then, air enters the space between the heating component 146 and the tar absorbing pad 419 through the air tube 152 and the through hole 1504. At this time, some e-liquid is vaporized by heating, and the airflow brings smoke formed by vaporizing the e-liquid into the airflow channel 1433 through the side end opening 1505, and the smoke enters the user's mouth through corresponding through holes on the upper tube 1431 and a vaping cap 142, thereby forming the airflow tube channel f2 to achieve a smoking action. It should be noted that during a vaping process, the air also enters the air tube 152 through the airflow channel f1.

In some embodiments of the present application, referring back to FIG. 2A, when the cartridge 11 is not inserted into the cigarette rod 12, there is no load between the pogo pin 1621 and the pogo pin 1622, and the main control module 166 detects that a high level exists between the pogo pin 1621 and the pogo pin 1622. As shown in FIG. 2B, when the cartridge 11 is inserted into the cigarette rod 12, the pogo pin 1621 and the pogo pin 1622 are electrically connected to the contact pad of the PCB module 151, that is, a current loop is formed between the PCB module 151 as a load and the pogo pin 1621 and the pogo pin 1622. In this case, because the PCB module 151 as a load may divide a voltage, the main control module 166 detects that a low level exists between the pogo pin 1621 and the pogo pin 1622, and the main control module 166 drives the indicator light 126 and the motor 122 to operate in the alerting mode. The alerting mode is: the indicator light 126 is turned on after the cartridge 11 and the cigarette rod 12 are engaged, and gradually goes out; and after the cartridge 11 and the cigarette rod 12 vibrates once after being engaged for 0.5 s, with a vibration time of 40 ms. The alerting mode is not limited thereto, which can be set according to practical conditions. In this way, the user can be reminded and informed that the cartridge 11 and the cigarette rod 12 have been engaged and can be used normally. In some embodiments of the present application, the main control module 166 may also determine that the cartridge 11 and the cigarette rod 12 have not been engaged when an output level of the connection circuit formed by the pogo pin 1621 and the pogo pin 1622 of the cigarette rod 12 is detected to be a low level, and determine that the cartridge 11 and the cigarette rod 12 have been engaged when the output level of the connection circuit is detected to be a high level.

When the user determines, according to the indicator light 126 and the motor 122, that the electronic cigarette 11 has been engaged, the user may start a normal vaping action.

When the user does not perform an inhalation or vaping action, the airflow sensor 121 does not detect the airflow change, and the airflow sensor 121 outputs a low level. When the user performs the inhalation or vaping action, the airflow sensor 121 detects the airflow, and the output level of the airflow sensor 121 changes from a low level to a high level. The main control module 166 outputs a voltage through the pogo pin 1621 and the pogo pin 1622 when receiving a signal indicating that the output level of the airflow sensor 121 changes from a low level to a high level, and provides the output voltage to the heating component 146 via the contact pad of the PCB module 151, the elastic piece 1481, the elastic piece 1482, the pin 1471, and the pin 1472, so that the heating component 146 performs heating, and the e-liquid in contact with the heating component 146 is vaporized. In addition, when the user vapes, air enters the cartridge 11 through the air tube 152, and the smoke in the vaporized state is fed to the user's mouth through the airflow channel, thereby completing an action of smoking once. When the smoking action is stopped, the airflow change in the electronic cigarette 10 stops, the airflow sensor 121 does not detect an airflow change, and the output level of the airflow sensor 121 changes from a high level to a low level. In this case, the main control module 166 controls disconnecting the output voltage between the pogo pin 1621 and the pogo pin 1622 after obtaining the signal indicating that the output level changes from the high level to the low level, that is, the heating component 146 stops heating. The main control module 166 records a start time t2 at which the high level is generated when the output level of the airflow sensor 121 is detected to change from the low level to the high level, and records a start time t3 at which the low level is generated when the output level of the airflow sensor 121 is detected to change from the high level to the low level next time. A time T2=t3−t2 for which the user takes one puff, where t3 is greater than t2. The main control module 166 performs counting and increases a count value C1 when T2 is greater than a preset threshold t4, for example, may increase the count value by 1. t4 may be set to 1 s, but is not limited thereto. If the user keeps performing the vaping action, when the count value C1 within time T3 is greater than a preset threshold n, the main control module 166 drives the motor 122 to operate in the alerting mode. The alerting mode is: the motor 122 vibrates. For example, when the count value C1 is greater than 15 within 10 minutes of T3, the main control module 166 may drive the motor 122 to vibrate once for a short time for one second after the 15th puff with a vibration time of 40 ms, thereby effectively alerting the user to control the vaping amount and prevent excessive vaping.

In some embodiments of the present application, the airflow sensor 121 may also output a low level when the airflow is detected, and outputs a high level when no airflow is detected. The main control module 166 may determine whether the user is smoking according to the level information that has different logic levels and output by the airflow sensor 121, and a specific determining manner is not limited to the foregoing.

In some embodiments of the present application, the main control module 166 stops the power supply of the battery 127 to the heating component 146 when T2 is greater than t5, so that the heating component 146 stops being heated. For example, the main control module 166 stops the power supply of the battery 127 to the heating component 146 when T2 is greater than 5 s, so that the heating component 146 stops being heated. In this way, the user can be prevented from smoking excessively.

In some embodiments of the present application, after the cartridge 11 and the cigarette rod 12 are engaged, the main control module 166 detects data information of the authentication circuit 112 electrically connected to the pogo pin 1623 in the PCB module 151. In some embodiments, the authentication circuit 112 includes a resistor that indicates flavor information of the cartridge 11, that is, different resistance values correspond to different flavors of the cartridge. For example, when the resistance is 2 ohms, it indicates that the cartridge 11 with a grapefruit-flavor is engaged with the cigarette rod 12. When the resistance is 4 ohms, it indicates that the cartridge 11 with a mint-flavor is engaged with the cigarette rod 12. It should be noted that a resistance value of a specific resistor and the flavor of the corresponding cartridge 11 are not limited thereto, which can be determined according to practical conditions. When the main control module 166 detects that the resistance of the resistor connected to the pogo pin 1623 is 2 ohms, it indicates that the cartridge 11 is the cartridge with a grapefruit-flavor.

In some embodiments of the present application, the authentication circuit 112 includes an encryption chip (not shown in the figure). The encryption chip stores encrypted data information of the cartridge 11, the data information including a unique ID number, a flavor of the cartridge, an amount of tar of the cartridge, and the like. The main control module 166 includes a decryption module corresponding to the encryption chip, and the decryption module includes a decryption chip. The decryption module is configured to decrypt the encrypted information when the cartridge 11 and the cigarette rod 12 are in the engaged state, send or transmitting decryption success information when the decryption is successful, and transmit decryption failure information when the decryption fails. After the decryption success information is received, the main control module 166 supplies power to the main control module 166 between the battery 127 and the heating circuit 111 to drive the indicator light 126 to flash three times and drive the motor 123 to vibrate for a short time three times. The main control module 166 enables a Bluetooth mode and transmits a broadcast signal by the antenna 170 after successfully decrypting the encrypted data information obtained from the encryption chip.

In some embodiments of the present application, the main control module 166 does not respond to changes in voltage or current between the pogo pin 1621 and the pogo pin 1622 upon receiving the decryption failure information. In some embodiments of the present application, the main control module 166 responds to changes in voltage or current between the pogo pin 1621 and the pogo pin 1622 upon receiving the decryption success information. In some embodiments of the present application, the main control module 166 does not respond to level information output by the airflow sensor 121 upon receiving the decryption failure information. In some embodiments of the present application, the main control module 166 responds to level information output by the airflow sensor 121 upon receiving the decryption success information.

In some embodiments of the present application, the main control module 166 obtains an acceleration value of an acceleration sensor 129, and determines a downtilt angle of the cartridge 11 according to the obtained acceleration value. As shown in FIG. 18, when the electronic cigarette 10 is placed horizontally, that is, the electronic cigarette 10 as shown in the state A. A downtilt angle determined by the main control module 166 is 0°, and in this case, the main control module 166 does not output any action instruction. When the electronic cigarette 10 is placed obliquely and a mouthpiece 141 is inclined downward, the main control module 166 determines that the downtilt angle is not less than a preset threshold α. α may be set to 20° and is saved or stored in a memory 124, but is not limited thereto. For the electronic cigarette 10 in the state B in FIG. 18, when the user vapes via the electronic cigarette 10 and tilts the mouthpiece 141 downward, it may be determined that the user is vaping via the electronic cigarette 10 in an inversed manner. However, because the mouthpiece 141 of the electronic cigarette 10 being inclined downward causes the e-liquid in the storage compartment 1434 not to penetrate into the heating component 146 through the heat-conducting top cap 144 and the heat-conducting silica gel 145 as a result of gravity influence. Therefore, when the user vapes the electronic cigarette in an inversed manner for too long, the e-liquid in the heating component 146 is dried out, causing the dry burning of the heating component 146 with a burnt flavor.

Therefore, when the electronic cigarette 10 is placed obliquely and the mouthpiece 141 is tilted downward, the main control module 166 determines that the downtilt angle is not less than a preset threshold α, and also detects that the output level of the airflow sensor 121 is a high level. In addition, when a vaping time T2 is greater than the preset threshold t4, the main control module 166 drives the motor 122 to vibrate in a fourth driving mode. The fourth driving mode is: driving the motor 122 to vibrate three times, a vibration time being 40 ms each time. Therefore, the user is alerted or informed to avoid the burnt flavor generated by the dry burning of the heating component 146 caused by excessively long vaping time inversely, thereby improving user experience. In some embodiments of the present application, the tilt angle determined by the main control module 166 may be a positive value or a negative value, the positive value and the negative value being used to indicate different downtilt directions. The positive value indicates that the mouthpiece 141 is tilted down, which is an inverse vaping state; and the negative value indicates that the mouthpiece 141 is tilted up, which is a normal use state.

In some embodiments of the present application, the main control module 166 enables the wireless communication function when the acceleration value of the acceleration sensor 129 is detected to be greater than the preset threshold a1, that is, transmits the broadcast signal by the antenna 170. The wireless communication function may be a Bluetooth function, and the antenna 170 may be a Bluetooth antenna, but is not limited thereto, as described above, which may be selected according to a specific situation. In addition, the main control module 166 drives the indicator light 126 in a third driving mode, the third driving mode being that the indicator light 126 flashes 15 times, to remind the user that the Bluetooth mode of the electronic cigarette 10 has been enabled. In addition, if the acceleration value is detected to be greater than the preset threshold value again within the preset time, that is, the user performs the shaking action again, the main control module 166 continues to drive the indicator light in the third driving mode. After the user learns that the Bluetooth mode of the electronic cigarette 10 is enabled, the user may perform Bluetooth matching with the electronic cigarette via a mobile phone to obtain the user smoking information and related data information of the cartridge 11 of the electronic cigarette 10.

Throughout the specification, references to "embodiment", "part of embodiments", "one embodiment", "another example", "example", "specific example" or "part of examples" mean that at least one embodiment or example of the present application includes specific features, structures, materials or characteristics described in the embodiment or example. Thus, the descriptions appear throughout the specification, such as "in some embodiments", "in an embodiment", "in one embodiment", "in another example", "in one example", "in a specific example" or "an example", which does not necessarily refer to the same embodiment or example in the present application.

As used herein, space-related terms such as "under", "below", "lower portion", "above", "upper portion", "lower portion", "left side", "right side", and the like may be used herein to simply describe a relationship between one element or feature and another element or feature as shown in the figures. In addition to orientation shown in the figures, space-related terms are intended to encompass different orientations of the device in use or operation. An apparatus may be oriented in other ways (rotated 90 degrees or at other orientations), and the space-related descriptors used herein may also be used for explanation accordingly. It should be understood that when an element is "connected" or "coupled" to another element, the element may be directly connected to or coupled to another element, or an intermediate element may exist.

As used herein, the terms "approximately", "basically", "substantially", and "about" are used to describe and explain small variations. When used in combination with an event or a situation, the terms may refer to an example in which an event or a situation occurs accurately and an example in which the event or situation occurs approximately. As used herein with respect to a given value or range, the term "about" generally means in the range of ±10%, ±5%, ±1%, or ±0.5% of the given value or range. The range may be indicated herein as from one endpoint to another endpoint or between two endpoints. Unless otherwise specified, all ranges disclosed herein include endpoints. The term "substantially coplanar" may refer to two surfaces within a few micrometers (m) positioned along the same plane, for example, within 10 μm, within 5 μm, within 1 μm, or within 0.5 μm located along the same plane. When reference is made to "substantially" the same numerical value or characteristic, the term may refer to a value within ±10%, ±5%, ±1%, or ±0.5% of the average of the values.

As used herein, the terms "approximately", "basically", "substantially", and "about" are used to describe and explain small variations. When used in combination with an event or a situation, the terms may refer to an example in which an event or a situation occurs accurately and an example in which the event or situation occurs approximately. For example, when being used in combination with a value, the term may refer to a variation range of less than or equal to ±10% of the value, for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, if a difference between two values is less than or equal to ±10% of an average value of the value (for example, less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%), it could be considered that the two values are "substantially" the same. For example, being "substantially" parallel may refer to an angular variation range of less than or equal to ±10° with respect to 0°, for example, less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°. For example, being "substantially" perpendicular may refer to an angular variation range of less than or equal to ±10° with respect to 90°, for example, less than or equal to ±5°, less than or equal to ±4°, less than or equal to ±3°, less than or equal to ±2°, less than or equal to ±1°, less than or equal to ±0.5°, less than or equal to ±0.1°, or less than or equal to ±0.05°.

As used herein, singular terms "a", "an", and "said" may include plural referents unless the context clearly dictates otherwise. In the description of some embodiments, assemblies provided "on" or "above" another assembly may encompass a case in which a previous assembly is directly on a latter assembly (for example, in physical contact with the latter assembly), and a case in which one or more intermediate assemblies are located between the previous assembly and the latter assembly.

Unless otherwise specified, space descriptions such as "above", "below", "up", "left", "right", "down", "top portion", "bottom portion", "vertical", "horizontal", "side face", "higher than", "lower than", "upper portion", "on", "under", "downward", etc. are indicated relative to the orientation shown in the figures. It should be understood that the space descriptions used herein are merely for illustrative purposes, and actual implementations of the structures described herein may be spatially arranged in any orientation or manner, provided that the advantages of embodiments of the present invention are not deviated due to such arrangement.

Although the illustrative embodiments have been shown and described, it should be understood by those skilled in the art that the above embodiments cannot be interpreted as limitations to the present application, and the embodiments can be changed, substituted and modified without departing from the spirit, principle and scope of the present application.

What is claimed is:

1. An electronic vaporizer device body, configured to be used in combination with an electronic vaporizer, the electronic vaporizer device body comprising:
   a power supply, configured to supply power;
   an airflow sensor, configured to detect an airflow change and output first level information; and
   a main control circuit, electrically connected to the airflow sensor and configured to control, according to the first level information, the power supply to supply or interrupt power to the electronic vaporizer;
   wherein the main control circuit controls an alerting device to operate in a first mode when a count value within a second preset time is detected to be greater than a preset threshold.

2. The electronic vaporizer device body according to claim 1, wherein the airflow sensor outputs the first level information having a first logic level when an airflow is detected, and the main control circuit controls the power supply to supply power to the electronic vaporizer upon receiving the first level information having the first logic level.

3. The electronic vaporizer device body according to claim 2, wherein the airflow sensor outputs the first level information having a second logic level when no airflow is detected, and the main control circuit controls the power supply to interrupt power to the electronic vaporizer upon receiving the first level information having the second logic level.

4. The electronic vaporizer device body according to claim 3, wherein the main control circuit increases a count value when a time interval between receiving the first level information having the first logic level and subsequent receiving of the first level information having the second logic level is detected to be greater than a first preset time.

5. The electronic vaporizer device body according to claim 3, wherein the main control circuit controls the power supply to interrupt power to the electronic vaporizer when a time interval between receiving the first level information having the first logic level and subsequent receiving of the first level information having the second logic level is detected to be greater than a third preset time.

6. The electronic vaporizer device body according to claim 3, the first logic level is a high level, and the second logic level is a low level.

7. The electronic vaporizer device body according to claim 3, the first logic level is a low level, and the second logic level is a high level.

8. The electronic vaporizer device body according to claim 3, the alerting device comprises one or any combination of the following: a motor and an indicator light.

9. An electronic vaporizer device, comprising an electronic vaporizer device body configured to be used in combination with an electronic vaporizer, the device vaporizer device body comprising:
   a power supply, configured to supply power;
   an airflow sensor, configured to detect an airflow change and output first level information; and
   a main control circuit, electrically connected to the airflow sensor and configured to control, according to the first level information, the power supply to supply or interrupt power to the electronic vaporizer;
   wherein the main control circuit controls an alerting device to operate in a first mode when a count value within a second preset time is detected to be greater than a preset threshold.

10. An operation method, applied to an electronic vaporizer device body, the method comprising:
    detecting an airflow change and outputting first level information by an airflow sensor; and
    controlling, by a main control circuit according to the first level information, a power supply to supply or interrupt power to an electronic vaporizer;
    wherein the main control circuit controls an alerting device to operate in a first mode when a count value within a second preset time is detected to be greater than a preset threshold.

11. The method according to claim 10, wherein the airflow sensor outputs the first level information having a first logic level when an airflow is detected, and the main control circuit controls the power supply to supply power to the electronic vaporizer upon receiving the first level information having the first logic level.

12. The method according to claim 11, wherein the airflow sensor outputs the first level information having a second logic level when no airflow is detected, and the main control circuit controls the power supply to interrupt power to the electronic vaporizer upon receiving the first level information having the second logic level.

13. The method according to claim 12, wherein the main control circuit increases a count value when a time interval between receiving the first level information having the first logic level and subsequent receiving of the first level information having the second logic level is detected to be greater than a first preset time.

14. The method according to claim 12, wherein the main control circuit controls the power supply to interrupt power to the electronic vaporizer when a time interval between receiving the first level information having the first logic level and subsequent receiving of the first level information having the second logic level is detected to be greater than a third preset time.

15. The method according to claim 12, wherein the first logic level is a high level, and the second logic level is a low level.

16. The method according to claim 12, wherein the first logic level is a low level, and the second logic level is a high level.

* * * * *